United States Patent [19]
Schwartz et al.

[11] Patent Number: 6,034,140
[45] Date of Patent: Mar. 7, 2000

[54] BIORESORBABLE COMPOSITIONS OF CARBOXYPOLYSACCHARIDE POLYETHER INTERMACROMOLECULAR COMPLEXES AND METHODS FOR THEIR USE IN REDUCING SURGICAL ADHESIONS

[75] Inventors: Herbert E. Schwartz; John M. Blackmore, both of Redwood City, Calif.

[73] Assignee: FzioMed, Inc., San Luis Obispo, Calif.

[21] Appl. No.: 09/023,097

[22] Filed: Feb. 13, 1998

Related U.S. Application Data

[62] Division of application No. 08/877,649, Jun. 17, 1997, Pat. No. 5,906,997.
[51] Int. Cl.$^7$ .......................... A61K 31/715; A61K 47/00
[52] U.S. Cl. .......................... 514/781; 536/54; 536/56; 536/57; 536/58; 536/59; 514/944; 600/556
[58] Field of Search .............................. 514/54, 56, 57, 514/58, 59, 944, 781; 600/556

[56] References Cited

U.S. PATENT DOCUMENTS

| | | | |
|---|---|---|---|
| 3,064,313 | 11/1962 | Butler | 18/57 |
| 3,328,259 | 6/1967 | Anderson | 167/84 |
| 3,387,061 | 6/1968 | Smith et al. | 260/874 |
| 4,024,073 | 5/1977 | Shimuzu et al. | 252/316 |
| 4,141,973 | 2/1979 | Balazs | 424/180 |
| 4,181,718 | 1/1980 | Mason et al. | 424/180 |
| 4,442,258 | 4/1984 | Sumakawa et al. | 524/767 |
| 4,616,644 | 10/1986 | Saferstein et al. | 128/156 |
| 4,684,558 | 8/1987 | Keusch et al. | 428/40 |
| 4,713,243 | 12/1987 | Schiraldi et al. | |
| 4,768,523 | 9/1988 | Cahalan et al. | 128/785 |
| 4,772,419 | 9/1988 | Malson et al. | 252/315.1 |
| 4,853,374 | 8/1989 | Allen | 514/57 |
| 4,937,254 | 6/1990 | Sheffield et al. | 514/420 |
| 4,937,270 | 6/1990 | Hamilton et al. | 514/777 |
| 4,983,585 | 1/1991 | Pennell et al. | 514/57 |
| 5,017,229 | 5/1991 | Burns et al. | 106/162 |
| 5,068,225 | 11/1991 | Pennell et al. | 514/57 |
| 5,080,893 | 1/1992 | Goldberg et al. | 514/57 |
| 5,093,319 | 3/1992 | Higham et al. | 514/55 |
| 5,140,016 | 8/1992 | Goldberg et al. | 514/57 |
| 5,156,839 | 10/1992 | Pennell et al. | 424/78.37 |
| 5,266,326 | 11/1993 | Barry et al. | 424/423 |
| 5,354,790 | 10/1994 | Keusch et al. | 523/300 |
| 5,356,883 | 10/1994 | Kuo et al. | 514/54 |
| 5,502,081 | 3/1996 | Kuo et al. | 514/777 |
| 5,532,221 | 7/1996 | Huang et al. | 514/53 |
| 5,621,093 | 4/1997 | Swann et al. | 536/55.2 |
| 5,681,873 | 10/1997 | Norton et al. | 523/115 |

FOREIGN PATENT DOCUMENTS

| | | |
|---|---|---|
| 0 138 572 A2 | 4/1985 | European Pat. Off. |
| 0 193 510 A1 | 9/1986 | European Pat. Off. |
| 0 265 561 A1 | 10/1986 | European Pat. Off. |
| WO 84/03302 | 8/1984 | WIPO |
| WO 86/00912 | 2/1986 | WIPO |
| WO 89/02445 | 3/1989 | WIPO |
| WO 90/10020 | 9/1990 | WIPO |

OTHER PUBLICATIONS

Elkins, et al,. Adhesion prevention by solutions of sodium carboxymethylcellulose in the rat. I. Fertility and Sterility, vol. 41, No. 6, 926–298, Jun. 1984.

Elkins, et al., Adhesion prevention by solutions of sodium carboxymethylcellulose in the rat. II, Fertility and Sterility, vol. 41, No. 6, 929–932, Jun. 1984.

Wiseman, *Polymers for the Prevention of Surgical Adhesions*, Johnson & Johnson Medical, Inc., Arlington, Texas, 369–421.

Merrill, *Poly(Ethylene Oxide) and Blood Contact, A Chronicle of One Laboratory*, 199–229.

Chaikof, Platelet Interaction with Poly(ethylene Oxide) Networks, AIChE Journal, vol. 36, No. 7, 994–1002, Jul. 1990.

Bottenberg, et al., Development and Testing of Bioadhesive, Fluoride–containing Slow–release Tablets for Oral Use, J. Pharm. Pharmacol., 43:457–464, 1991.

Amiji, Permeability and blood compatibility properties of chitosan–poly(ethylene oxide) blend membranes for haemodialysis, Biomaterials, 16, 593–599, 1995.

Dieckman, et al., Carboxymethylcellulose in the Free Acid Form, Industrial and Engineering Chemistry, vol. 45, No. 10, 2287–2290.

Gurny, et al., Bioadhesive intraoral release systems: design, testing and analysis, Biomaterials, vol. 5, 336–340, 1984.

Chen, et al., Compositions Producing Adhesion Through Hydration, 163–181.

Kulicke, et al., Characterization of aqueous carboxymethylcellulose solutions in terms of their molecular structure and its influence on rheological behavior, Polymer, vol. 37, No. 13, 2723–2731, 1996.

(List continued on next page.)

*Primary Examiner*—Gary L. Kunz
*Attorney, Agent, or Firm*—Fliesler Dubb Meyer & Lovejoy LLP

[57] ABSTRACT

The present invention relates to improved methods for making and using bioadhesive, bioresorbable, anti-adhesion compositions made of intermacromolecular complexes of carboxyl-containing polysaccharides and polyethers, and to the resulting compositions. The polymers are associated with each other, and are then either dried or are used as fluids. Bioresorbable, bioadhesive, anti-adhesion compositions are useful in surgery to prevent the formation of post-surgical adhesions. The compositions are designed to breakdown in-vivo, and thus be removed from the body. Membranes are inserted during surgery either dry or optionally after conditioning in aqueous solutions. The anti-adhesion, bioadhesive, bioresorptive, antithrombogenic and physical properties of such membranes can be varied as needed by carefully adjusting the pH of the polymer casting solutions, polysaccharide composition, the polyether composition, or by conditioning the membranes prior to surgical use. Bi- or multi-layered membranes can be made and used to provide further control over the physical and biological properties of antiadhesion membranes. Antiadhesion compositions may also be used to deliver drugs to the surgical site and release them locally.

24 Claims, 7 Drawing Sheets

OTHER PUBLICATIONS

Ohno, et al., Interpolymer Complex Formation of Polysaccharides with Poly(ethylene oxide) or Poly(1–vinyl–2–pyrrolidone) through Hydrogen Bond, Makromol. Chem., Rapid Commun., 2, 511–515, 1981.

*Acqualon, Sodium Carboxymethylcellulose, Physical and Chemical Properties*, Hercules, Inc., 1–27.

Didishelm, et al., Hematologic and Coagulation Studies in Various Animal Species, J. Lab. & Clin. Med., 866–875, Jun. 1959.

Harris, et al., Analysis of the Kinetics of peritoneal adhesion formation in the rat and evaluation of potential antiadhesive agents, Surgery, 663–669, Jun. 1995.

Becker, et al., Prevention of Postoperative Abdominal Adhesions by a Sodium Hyaluronate–based Bioresorbable Membrane: A Prospective, Randomized, Double–Blind Multicenter Study, Journal of American College of Surgeons, vol. 183, 297–306, Oct. 1996.

INTERCEED (TC7) Adhesion Barrier Study Group, Prevention of postsurgical adhesions by INTERCEED (TC7), *an absorbable adhesion barrier: a prospective, randomized multicenter clinical study, Fertility and Sterility, vol. 51, No. 6, 933–938, Jun. 1989.

Diamond, et al., Reduction of adhesions after uterine myomectomy by Seprafilm* membrane (HAL–F): a blinded, prospective, randomized, multicenter clinical study, Fertility and Sterility, vol. 66, No. 6, 904–910, Dec. 1996.

Sung, et al., Swelling properties of hyaluronic acid ester membranes, Journal of Membrane Science, 92, 157–167, 1994.

Braun, Poly(Ethylene Oxide), Union Carbide Corporation, Union Carbide Chemical and Plastics Company, Inc., Specialty Chemicals Division, (Reprinted from Handbook of Water–Soluble Gums and Resins), pp. 19–1–19–33.

*Polyox Water–soluble Resins*, Association Compounds, Union Carbide Chemicals Division, p. 22, 1991.

*Sepra film™ Bioresorbable Membrane, Product Monograph for the Reduction of Postsurgical Adhesions*, Genzyme Corporation, 1–29, 1996.

Kitano, et al., Viscous Carboxymethylcellulose in the Prevention of Epidural Scar Formation, Spine, vol. 16, No. 7, Jul. 1991.

*Hercules Cellulose Gum, Sodium Carboxymethylcellulose, Chemical and Physical Properties*, Hercules, Inc., 1–31, 1984.

Takayama, et al., Effect of Interpolymer Complex Formation on Bioadhesive Property and Drug Release Phenomenon of Compressed Tablet Consisting of Chitosan and Sodium Hyaluronate, Chem. Pharm. Bull., 38(7), 1993–1997, 1990.

Aurora, et al., Pathology of Peritoneal Adhesions—An Experimental Study, Indian J. Med. Res., 62, 4, 539–544, Apr. 1974.

Harland, et al., Polyelectrolyte Gels, Properties, Preparation, and Applications, American Chemical Society Symposium Series, Nov. 11–16, 1990, 480.

Feddersen, et al., Sodium Carboxymethylcellulose, Industrial Gums, Polysaccharides and Their Derivatives, Third Edition, 537–579, 1993.

Steizer, et al., Carboxymethylcellulose, Handbook of Water–Soluble Gums and ResinsChapter 4, pp. 4–1–4–28, 1980.

Danishefsky, et al., Conversion of Carboxyl Groups of Mucopolysaccharides into Amides of Amino Acid Esters, Carbohyd. Res., 16, 199–205, 1971.

Park, et al, Test Methods of Bioadhesion, Bioadhesive drug delivery systems, Chapter 3, 26–168, 1990.

Tsuchida, et al., Interactions Between Macromolecules in Solution and Intermacromolecular Complexes, Advances Polymer Sciences, 45–122, 1982.

Anseth, et al., Mechanical properties of hydrogels and their experimental determination, Biomaterials, 17, 1647–1657, 1996.

Kofinas, et al., Development of methods for quantitative characterization of network morphology in pharmaceutical hydrogels, Biomaterials, Vo. 18, No. 20, 1361–1369.

FIG.−1

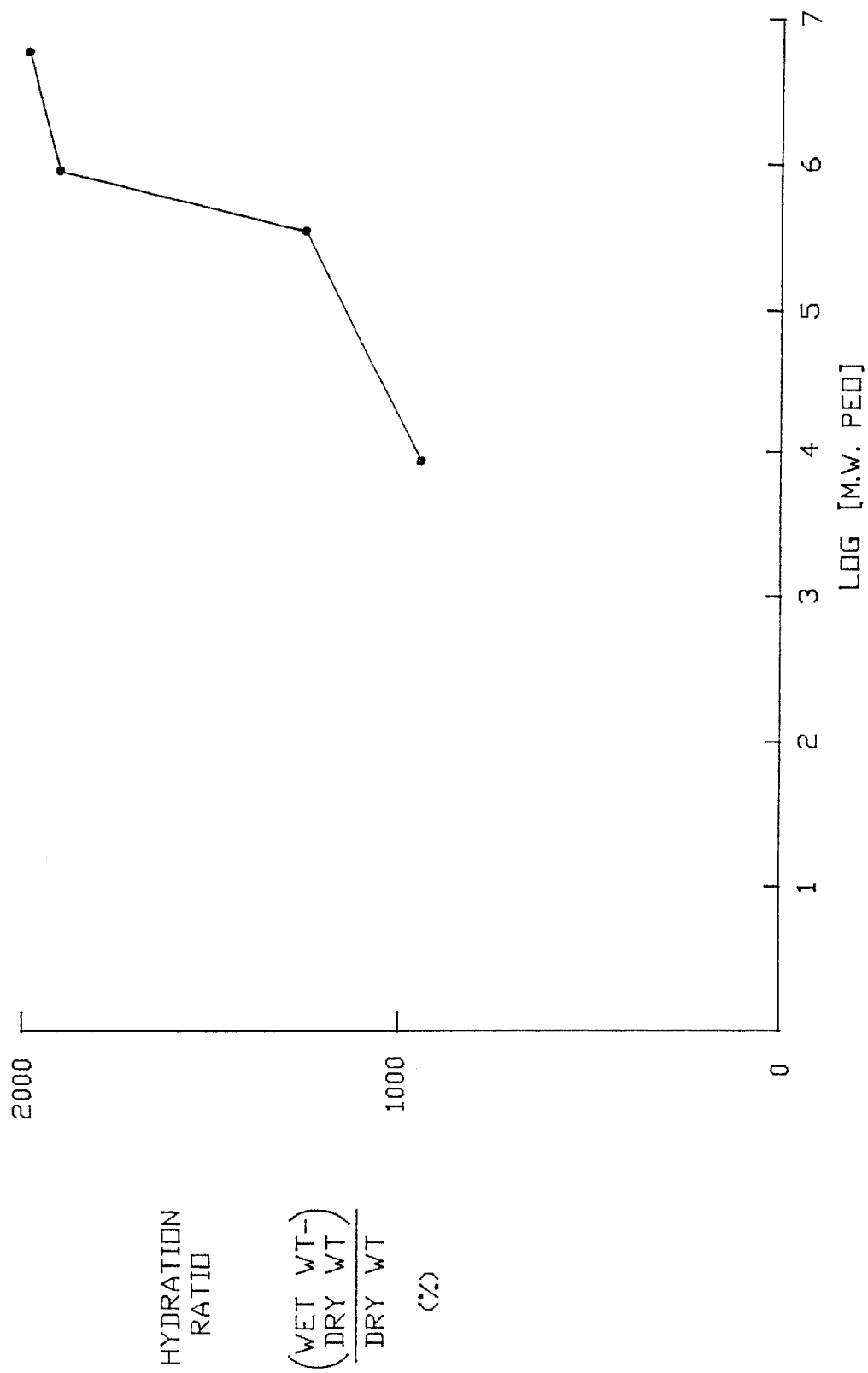

BIORESORBABLE COMPOSITIONS OF CARBOXYPOLYSACCHARIDE POLYETHER INTERMACROMOLECULAR COMPLEXES AND METHODS FOR THEIR USE IN REDUCING SURGICAL ADHESIONS

This application is a Division of Ser. No. 08/877,649, filed Jun. 17, 1997, now U.S. Pat. No. 5,906,997, issued May 25, 1999.

FIELD OF THE INVENTION

This invention relates generally to the manufacture of membranes comprising carboxypolysaccharide/polyether intermacromolecular complexes and the use of those membranes to prevent adhesions between tissues from forming after surgery. The membrane properties can be tailored to achieve desired degrees of adhesion prevention, bioresorbability, bioadhesiveness, and antithrombogenic effects.

BACKGROUND OF THE INVENTION

Adhesions are unwanted tissue growths occurring between layers of adjacent bodily tissue or between tissues and internal organs. Adhesions commonly form during the healing which follows surgical procedures, and when present, adhesions can prevent the normal motions of those tissues and organs with respect to their neighboring structures.

The medical and scientific communities have studied ways of reducing the formation of post-surgical adhesions by the use of high molecular weight carboxyl-containing biopolymers. These biopolymers can form hydrated gels which act as physical barriers to separate tissues from each other during healing, so that adhesions between normally adjacent structues do not form. After healing has substantially completed, the barrier is no longer needed, and should be eliminated from the body to permit more normal function of the affected tissues.

Several different types of biopolymers have been used for this purpose. For example, Balazs et al., U.S. Pat. No. 4,141,973 discloses the use of a hyaluronic acid (HA) fraction for the prevention of adhesions. However, because HA is relatively soluble and readily degraded in vivo, it has a relatively short half-life in vivo of 1 to 3 days, which limits its efficacy as an adhesion preventative.

Methyl cellulose and methyl cellulose derivatives are also known to reduce the formation of adhesions and scarring that may develop following surgery. (Thomas E. Elkins, et al., *Adhesion Prevention by Solutions of Sodium Carboxymethylcellulose in the Rat, Part I*, Fertility and Sterility, Vol. 41, No. 6, June 1984; Thomas E. Elkins, M.D. et al., *Adhesion Prevention by Solutions of Sodium Carboxymethylcellulose in the Rat, Part II*, Fertility and Sterility, Vol. 41. No. 6, June 1984. However, these solutions are rapidly reabsorbed by the body and disappear from the surgical site.

In addition to solutions of carboxyl-containing biopolymers, solutions of polyethers can also decrease the incidence of post-surgical adhesions. Pennell et al., U.S. Pat. No. 4,993,585 describes the use of polyethylene oxide in solutions of up to 15% to decrease formation of post-surgical adhesions. Pennell et al., U.S. Pat. No. 5,156,839 describes the use of mixtures of carboxymethylcellulose up to about 2.5% by weight, and polyethylene oxide, in concentrations of up to about 0.5% by weight in physiologically acceptable, pH neutral mixtures. Because of the neutral pH, these materials do not form association complexes, and thus, being soluble, are cleared from the body within a short period of time.

The above-described solutions have several disadvantages. First, they have short biological residence times and therefore may not remain at the site of repair for sufficiently long times to have the desired anti-adhesion effects.

Although the methods of manufacture of certain carboxypolysaccharide-containing membranes have been described, the membranes are poorly suited for use to prevent adhesions. Butler, U.S. Pat. No. 3,064,313 describes the manufacture of films made of 100% carboxymethylcellulose (CMC) with a degree of substitution of 0.5 and below, made insoluble by acidifying the solution to pH of between 3 and 5, and then drying the mixture at 70° C. to create a film. These films were not designed to be used as anti-adhesion barriers. Anderson, U.S. Pat. No. 3,328,259 describes making films of 100% carboxymethylcellulose and polyethylene oxide, alkali metal salts, and a plasticizing agent for use as external bandages. These materials are rapidly soluble in plasma and water and thus would have a very short residence time as an intact film. Therefore, these compositions are not suitable for alleviating surgical adhesions.

Smith et al., U.S. Pat. No. 3,387,061 describes insoluble association complexes of carboxymethylcellulose and polyethylene oxide made by lowering the pH to below 3.5 and preferably below 3.0, and then drying and baking the resulting precipitate (See Example XXXVIII). These membranes were not designed for surgical use to alleviate adhesions. Such membranes are too insoluble, too stiff, and swell to little to be ideal for preventing post-surgical adhesions. In addition, their excessive acidity would cause tissue inflammation.

Burns et al., U.S. Pat. No. 5,017,229 describes water insoluble films made of hyaluronic acid, carboxymethyl cellulose, and a chemical cross-linking agent. Because of the covalent cross-linking with a carbodiimide, these films need extensive cleaning procedures to get rid of the excess cross-linking agent; and because they are made without a plasticizer, they are too stiff and brittle to be ideally suited for preventing adhesions—they do not readily conform to the shapes of tissues and organs of the body.

Thus, there have been few successful antiadhesion membranes. D. Wiseman reviews the state of the art of the field in *Polymers for the Prevention of Surgical Adhesions, In: Polymeric Site-specific Pharmacotherapy*, A. J. Domb, Ed., Wiley & Sons, (1994). A currently available antiadhesion gel is made of ionically cross-linked hyaluronic acid. Huang et al., U.S. Pat. No. 5,532,221. Cross-linking is created by the inclusion of polyvalent cations, such as ferric, aluminum or chromium salts. Unfortunately, hyaluronic acid (either from natural sources or bioengineered) is quite expensive. Therefore, the prior art discloses no membranes ideally suited to the variety of surgical uses of the instant invention. Thus, there are several objects of the instant invention.

A first object is to provide compositions and methods which reduce the incidence of adhesion formation during and after surgery. This includes the prevention of de novo adhesion formation in primary or secondary surgery.

An additional object is to prevent reformation of adhesions after a secondary procedure intended to eliminate the de novo adhesions which had formed after a primary procedure.

Another object is to provide an inexpensive antiadhesion membrane which remains intact at the surgical site during the initial stages of critical wound healing.

Yet another object of the invention is to provide an antiadhesion membrane which can hydrate quickly in a controlled fashion to form an intact hydrogel.

An additional object of the invention is to provide an antiadhesion membrane which is resorbable and completely eliminated from the body.

A further object of the invention is to provide an antiadhesion membrane which has good handling characteristics during a surgical procedure, is conformable to a tissue, pliable, strong, and easy to mold to tissue surfaces, and possesses sufficient bioadhesiveness to ensure secure placement at the surgical site until the likelihood of adhesion formation is minimized.

Yet another objective of the invention is to provide an antiadhesion membrane with desired properties with drugs incorporated into the membrane, so that the drug can be delivered locally over a period of time to the surgical site.

To achieve these objectives, the instant invention involves carefully controlling the properties of antiadhesion membranes by closely regulating the pH, amounts of carboxyl residues and polyether within the carboxypolysaccharide/polyether association complex, to closely control the degree of association between the polymers. By carefully controlling the degree of intermolecular binding and amount of polyether, we can closely vary the physical properties of the membranes and therefore can optimize the antiadhesion, bioadhesive, bioresorptive, and antithrombogenic properties of the membranes to achieve the desired therapeutic results.

Too much hydration can result in an irreversible transformation of the membrane to a "loose gel" which will not stay in place or will disintegrate. In addition, too much swelling can create too much hydrostatic pressure which could adversely affect tissue and organ function. The membrane must be physiologically acceptable, be soft, have the desired degree of bioresorbability, have the desired degree of antithrombogenicity, and must be biologically inert.

SUMMARY OF THE INVENTION

One aspect of the invention is a composition made of an intermacromolecular association of a carboxypolysaccharide (CPS) and optionally a polyether (PE) which are useful for inhibiting post-surgical adhesions. Another aspect of the invention comprises methods of manufacturing complexes of CPS and PE which exhibit desired physical and biological properties.

Creation of complexes with desired properties is accomplished by varying the degree of bonding between the polymers. This variation in properties is accomplished by varying the pH of the casting solution (hereafter referred to as "the membrane pH"), the molecular weights of the polymers, the percentage composition of the polymer mixture, and/or the degree of substitution (d.s.) by carboxyl residues within the CPS. Additional variation in membrane properties is accomplished by conditioning membranes after their initial manufacture. Multi-layered membranes are also an aspect of the invention, with different layers selected to exhibit different properties.

Additionally, in accordance with some aspects of the invention, drugs can be included in the membranes to deliver pharmacological compounds directly to the tissues.

The materials are biocompatible, and are cleared from the body within a desired period of time, which can be controlled. The membranes are used to inhibit the formation of post-surgical adhesions.

Unlike the prior art, anti-adhesion compositions can be made having desired properties. Furthermore, conditioning of anti-adhesion membranes after their manufacture results in unexpected properties, which are advantageous for the use of the invention to alleviate post surgical adhesions.

BRIEF DESCRIPTION OF THE FIGURES

FIG. 7 shows the effect of changing the molecular weight of PEO on hydration or swelling of CMC/PEO membranes.

DETAILED DESCRIPTION OF THE PREFERRED EMBODIMENT

Definitions

Figure 1:
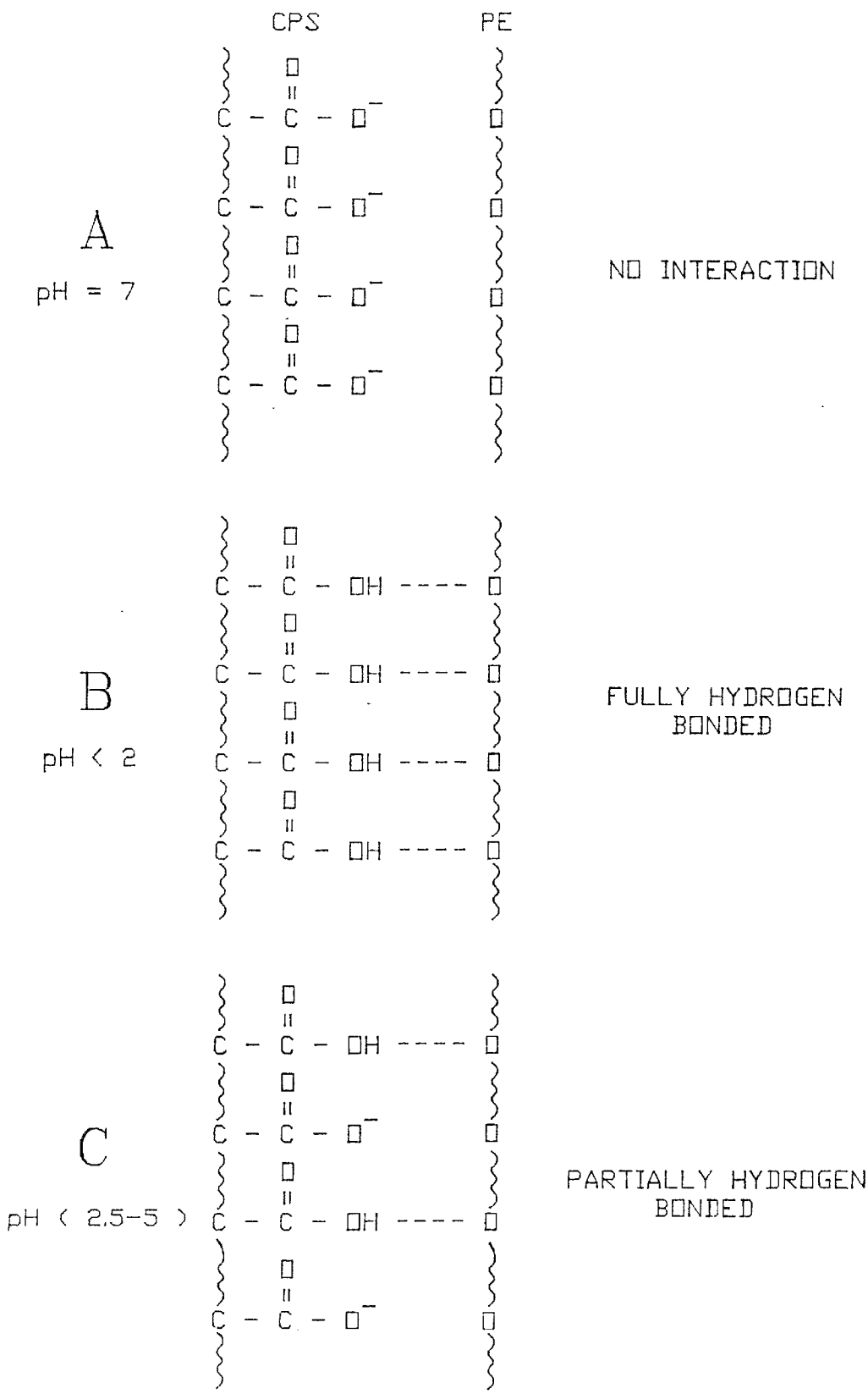
FIG. 1 is a schematic representation of a theory of formation of association complexes between carboxypolysaccharides and polyethers resulting from hydrogen bonding at different pHs.

Before describing the invention in detail, the following terms are defined as used herein.

The term "adhesion" means abnormal attachments between tissues and organs that form after an inflammatory stimulus such as surgical traum. The terms "adhesion prevention" and "anti-adhesion" means preventing or inhibiting the formation of post-surgical scar and fibrous bands between traumatized tissues, and between traumatized and nontraumatized tissues.

The term "association complex" or "intermacromolecular complex" means the molecular network formed between polymers containing CPS and/or PE.

The term "bioadhesive" means being capable of adhering to living tissue.

The term "bioresorbable" means being capable of being reabsorbed and eliminated from the body.

The term "biocompatible" means being physiologically acceptable to a living tissue and organism.

The term "carboxymethylcellulose" ("CMC") means a polymer composed of repeating cellobiose units, further composed of two anhydroglucose units (B-glucopyranose residues), joined by 1,4 glucosidic linkages. The cellobiose units are variably carboxylated.

The term "degree of substitution" ("d.s.") means the average number of carboxyl residues present per mole of cellobiose.

The term "discectomy" means a surgical operation whereby a ruptured vertebral disc is removed.

The term "endoscope" means a fiber optic device for close observation of tissues within the body, such as a laparoscope or arthroscope.

The term "fibrous tissue" means a scar or adhesions.

The term "hyaluronic acid" ("HA") means an anionic polysaccharide composed of repeat disaccharide units of N-acetylglucosamine and glucuronic acid. HA is a natural component of the extracellular matrix in connective tissue.

The term "hydration" (also "swelling") means the process of taking up solvent by a polymer solution.

The term "hydration ratio" (also "swelling ratio") means the wet weight of a hydrated membrane less the dry weight divided by the dry weight×100%.

The term "hydrogel" means a three-dimensional network of hydrophilic polymers in which a large amount of water is present.

The term "laminectomy" means a surgical procedure wherein one or more vertebral lamina are removed.

The term "laparoscope" means a small diameter scope inserted through a puncture wound in the abdomen, used for visualization during minimally invasive surgical procedures.

The term "membrane pH" means the pH of the casting solution from which the membrane is made.

The term "mesothelium" means the epithelium lining the pleural, pericardial and peritoneal cavities.

The term "peritoneum" means the serous membrane lining the abdominal cavity and surrounding the viscera.

The term "polyethylene oxide" means the non-ionic polyether polymer composed of ethylene oxide monomers.

The term "tissue ischemia" means deprivation of blood flow to living tissues.

DETAILED DESCRIPTION OF THE INVENTION

The present invention is directed to a method of reducing the formation of adhesions during and following surgery comprising the step of delivering to a wound an implantable, bioresorbable association complex of carboxypolysaccharides (CPS) and a polyether (PE). Complexes are generally made by mixing appropriate amounts and compositions of CPS and PE together in solution, then, optionally acidifying the solution to a desired pH to form an acidified association complex, and then if desired, by pouring the solution into a suitable flat surface and permitting the mixture to dry to form a membrane at either reduced (>0.01 Torr) or normal (about 760 Torr) atmospheric pressure. The association complex is placed between tissues which, during wound healing, would form adhesions between them. The complex remains at the site for different periods of time, depending upon its composition, method of manufacture, and upon post-manufacture conditioning. When the tissues have substantially healed, the complex then degrades and/or dissolves and is cleared from the body.

Membranes in accordance with the invention can be made with desired degrees of stiffness, different rates of bioresorbability, different degrees of bioadhesion, different degrees of anti-adhesion effectiveness and different degrees of antithrombogenic properties.

Although the exact mechanism of association complex formation is not completely known, one theory is that hydrogen bonding occurs between the carboxyl residues of the polysaccharide and the ether oxygen atoms of the polyether. See Dieckman et al., Industrial and Engineering Chemistry 45(10):2287–2290 (1953). FIG. 1 illustrates this theory. The pH of the polymer solution from which the membrane is cast (the "casting solution") is carefully titrated to an acidic pH by means of a suitable acid. The initially neutral, anionic polysaccharide carboxyl groups are converted into protonated, free carboxylic acid groups by the addition of the acid (e.g. hydrochloric acid) to the mixed polymer casting solution. The protonated carboxyl residues can subsequently bond electrostatically to the ether oxygen atoms of the polyether, thereby forming hydrogen bonds, a type of dipole-dipole interaction.

Decreasing the pH of the casting solution increases the number of protonated carboxyl residues, which increases the number of possible hydrogen bonds with the polyether. This strengthens the polymer network, and results in a stronger, more durable, less soluble and less bioresorbable membrane. On the other hand, if the casting solution is near neutral pH, the carboxyl groups on the carboxypolysaccharide are more negatively charged and thus repel both each other and the ether oxygen atoms of the PE, resulting in a weakly bonded gel with little or no structural integrity.

Figure 2:
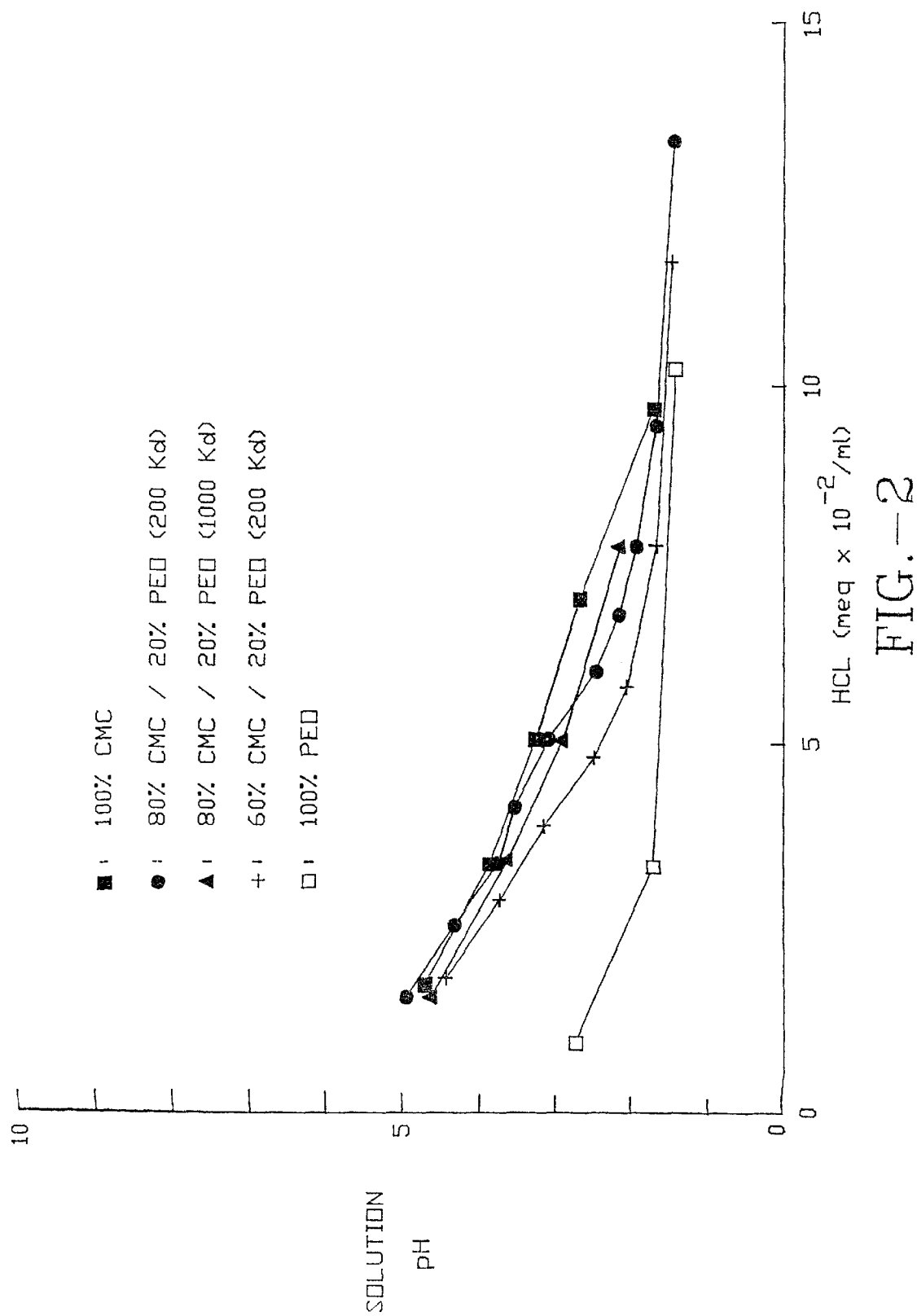
FIG. 2 shows the results of studies of pH titrations of the solutions made for casting CMC- and polyethylene oxide (PEO)-containing membranes.

For the purpose of illustration, three cases of such interactions can be distinguished as shown in FIG. 1. The figure shows a schematic representation of the possible intermolecular complexation in which four carboxymethyl groups from a carboxypolysaccharide (CPS) chain are aligned opposite to four ether oxygen atoms of a polyether (PE) chain. FIG. 1a shows the situation which would exist at a pH of about 7. At neutral pH, the carboxyl residues are dissociated, so no hydrogen bonded complex is formed between the ether oxygen atoms of the PE and the negatively charged carboxymethyl groups of CPS. FIG. 1b shows the situation which would exist at a pH of about 2. At low pH, most of the carboxyl residues are protonated, so most are hydrogen-bonded to the ether oxygen atoms of the PE. FIG. 1c shows the situation which would exist at a pH of approximately 3–5. At the $pK_a$ of the CPS of about 4.4, half of the carboxyl groups are protonated, and thus are hydrogen bonded to the corresponding ether oxygen atoms of the PE. Within this intermediate pH region, the degree of cross-linking can be carefully adjusted according to the present invention (FIG. 2).

Membranes made according to FIG. 1b are like those described by Smith et al. (1968). They lack the several key features of the ideal adhesion preventative membrane. The low pH membranes hydrate poorly. Further, they are rough to the touch, non-pliable, and are poorly soluble. Because they are insoluble, they would not be cleared from the body in a sufficiently short time period. Moreover, because of the high acidity of the casting solution, they deliver a relatively larger amount of acid to the tissue compared to more neutral pH membranes. Physiological mechanisms may have difficulty in neutralizing this acid load before tissue damage occurs. Thus, they can have poor biocompatability.

In contrast to the prior art membranes described above, the present invention teaches adhesion preventative membranes as schematically depicted in FIG. 1c. These membranes are made in an intermediate pH range, typically between approximately 3 and 5, so that the amount of cross-linking is neither too great, which would result in complexes which would not dissolve rapidly enough, nor too little, which would result in a complex which would disintegrate too rapidly. Furthermore, varying the pH of the casting solutions varies the rheological properties of the solution (Table 1), and varies the physical properties of the membranes made from those solutions (Table 2).

The above mechanism for formation of association complexes is not necessary to the invention. The results of our studies with CPS and PE describe the invention fully, without reliance upon any particular theory of the association between the components.

Manufacturing membranes from CPS/PE casting solutions requires only that the solution of CPS and PE can be handled easily. Dilute solutions (up to about 10% weight/ volume) of CPS are easy to handle, and solutions of about 2% CPS are easier to handle. Solutions of PEO up to about 20% (weight/volume) are possible to make and handle, and solutions of about 1% by weight are easy to handle.

The carboxypolysaccharide may be of any biocompatible sort, including but not limited to carboxymethyl cellulose (CMC), carboxyethyl cellulose, chitin, hyaluronic acid, starch, glycogen, alginate, pectin, carboxymethyl dextran, carboxymethyl chitosan, and glycosaminoglycans such as heparin, heparin sulfate, and chondroitin sulfate. Preferably, carboxymethyl cellulose or carboxyethyl cellulose is used. More preferably, carboxymethyl cellulose (CMC) is used. The molecular weight of the carboxypolysaccharide can vary from 100 kd to 10,000 kd. CPS in the range of from 600 kd to 1000 kd work well, and CPS of 700 kd works well, and is easily obtained commercially.

Similarly, the polyether used is not crucial. The preferred polyether of the present invention is polyethylene oxide (PEO). Whereas CMC sodium by itself has been used as an antiadhesion barrier in a gel formulation, CMC/PEO membranes have some unique properties useful for adhesion prevention.

Membranes made of CMC and PEO together are more flexible than membranes made of CMC alone, which are hard and stiff. The membranes may accordingly be manipulated during surgery to conform closely to the shape needed for close adherence to a variety of tissues. Further, the inclusion of PEO in the complex confers antithrombogenic properties which help prevent adhesions by decreasing the adherence of blood proteins and platelets to the membrane (Amiji, *Biomaterials,* 16:593–599 (1995); Merill, E. W., *PEO and Blood Contact in Polyethylene Glycol Chemistry-Biotechnical and Biomedical Applications,* Harris J. M. (ed), Plenum Press, NY, 1992; Chaikof et al., *A.I. Ch.E. Journal* 36(7):994–1002 (1990)). PEO-containing membranes impair the access of fibrin clots to tissue surfaces, even more so than a membrane containing CMC alone. Increasing flexibility of CMC/PEO membranes without compromising the tensile strength or flexibility improves the handling characteristics of the membrane during surgery. The molecular weight range of the polyether as used in this invention can vary from 5 kd to 8000 kd. Polyether in the range from 100 kd to 5000 kd work well and are readily available commercially.

Varying the ratio of the polysaccharide and polyether alters viscoelastic properties of the solutions (Tables 4, 5), and produces different degrees of adhesion prevention and antithrombogenic effects. Increasing the percentage of CPS increases the bioadhesiveness, but reduces the antithrombogenic effect. On the other hand, increasing the percentage of PE increases the antithrombogenic effect but decreases bioadhesiveness. The percentage of carboxypolysaccharide to polyether may be from 10% to 100% by weight, preferably between 50% and 90%, and most preferably should be 90% to 95%. Conversely, the percentage of polyether may be from 0% to 90%, preferably from 5% to 50%, and most preferably should be approximately 5% to 10%.

The tightness of the association and thus the physical properties of the association complex between the CPS and PE may be closely regulated. Decreasing the pH of the association complex increases the amount of hydrogen cross-linking. Similarly, increasing the degree of substitution of the carboxypolysaccharide in the membrane increases cross-linking within the association complex at any given pH, and thereby decreases the solubility and therefore the bioresorbability of the complex. Membranes made from low pH polymer solutions are generally harder and stiffer, dissolve more slowly, and therefore have longer residence times in tissues than do membranes made from solutions with higher pH or of hydrogels. Low pH polymer membranes are generally useful in situations where the period of adhesion formation may be long, or in tissues which heal slowly. Such situations may occur in recovery from surgery to ligaments and tendons, tissues which characteristically heal slowly. Thus, a long-lasting membrane could minimize the formation of adhesions between those tissues. However, low pH membranes are rough to the touch, crack easily when folded, and tend to shatter easily.

In contrast, membranes made from solutions with higher pH are more flexible and easier to use than membranes made from solutions with lower pH. They are more bioadhesive and biodegrade more rapidly than membranes made at lower pH, and are therefore more useful where the period of adhesion formation is short. These membranes feel smooth, and are pliable, and are capable of being folded without as much cracking or shattering compared to membranes made from solutions with low pH.

The pH of the association complex of the present invention may be between 1 and 7, preferably between 2 and 7, more preferably between 3 and 7, even more preferably between 3.5 and 6.0. For certain uses, a pH of about 4.1 is preferred, where there is a desirable balance between the bioadhesiveness, antiadhesion properties, the rates of bioresorbability and the biocompatability for most of the uses contemplated in the present invention.

Bioadhesiveness is defined as the attachment of macromolecules to biological tissue. Bioadhesiveness is important in preventing surgical adhesions because the potential barrier must not slip away from the surgical site after being placed there. Both CMC and PEO individually are bioadhesive (e.g., see Bottenberg et al., *J. Pharm. Pharmacol.* 43:457–464 (1991)). Like other polymers which are known to swell when exposed to water, CMC/PEO membranes are also bioadhesive.

Hydration contributes to bioadhesiveness of membranes (Gurney et al, *Biomaterials* 5:336–340 (1984); Chen et al., *Compositions Producing Adhesion Through Hydration, In: Adhesion in Biological Systems,* R. S. Manly (Ed.) Acad. Press NY (1970), Chapter 10). A possible reason for this phenomenon is that with increased hydration, more charges on the CMC become exposed, and therefore may be made available to bind to tissue proteins. However, excessive hydration is detrimental to bioadhesion. Thus, a means of controlling the bioadhesiveness of membranes is to control their hydration properties.

Figure 3:
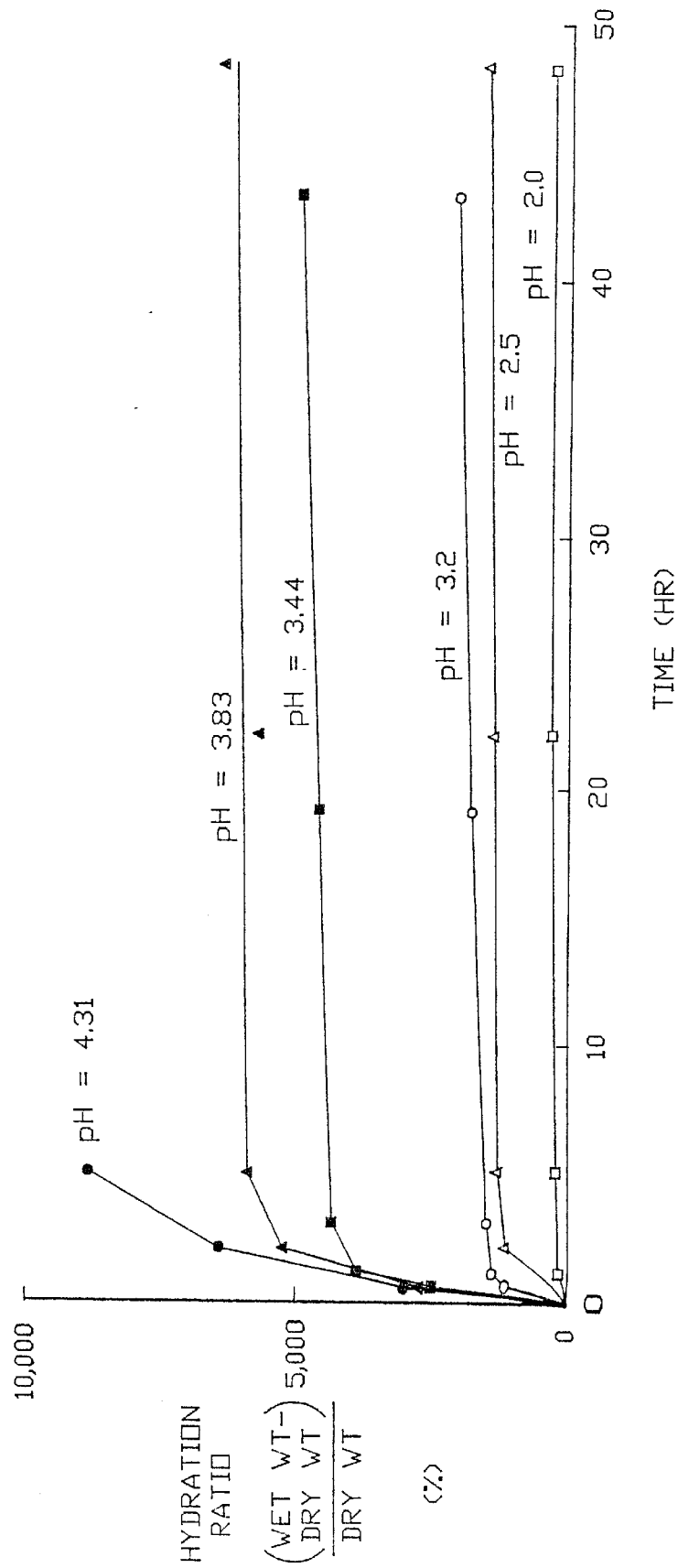
FIG. 3 shows the time course of hydration or swelling of CMC/PEO membranes made from casting solutions at different pHs, from 2.0 to 4.31 at room temperature.
Figure 4:
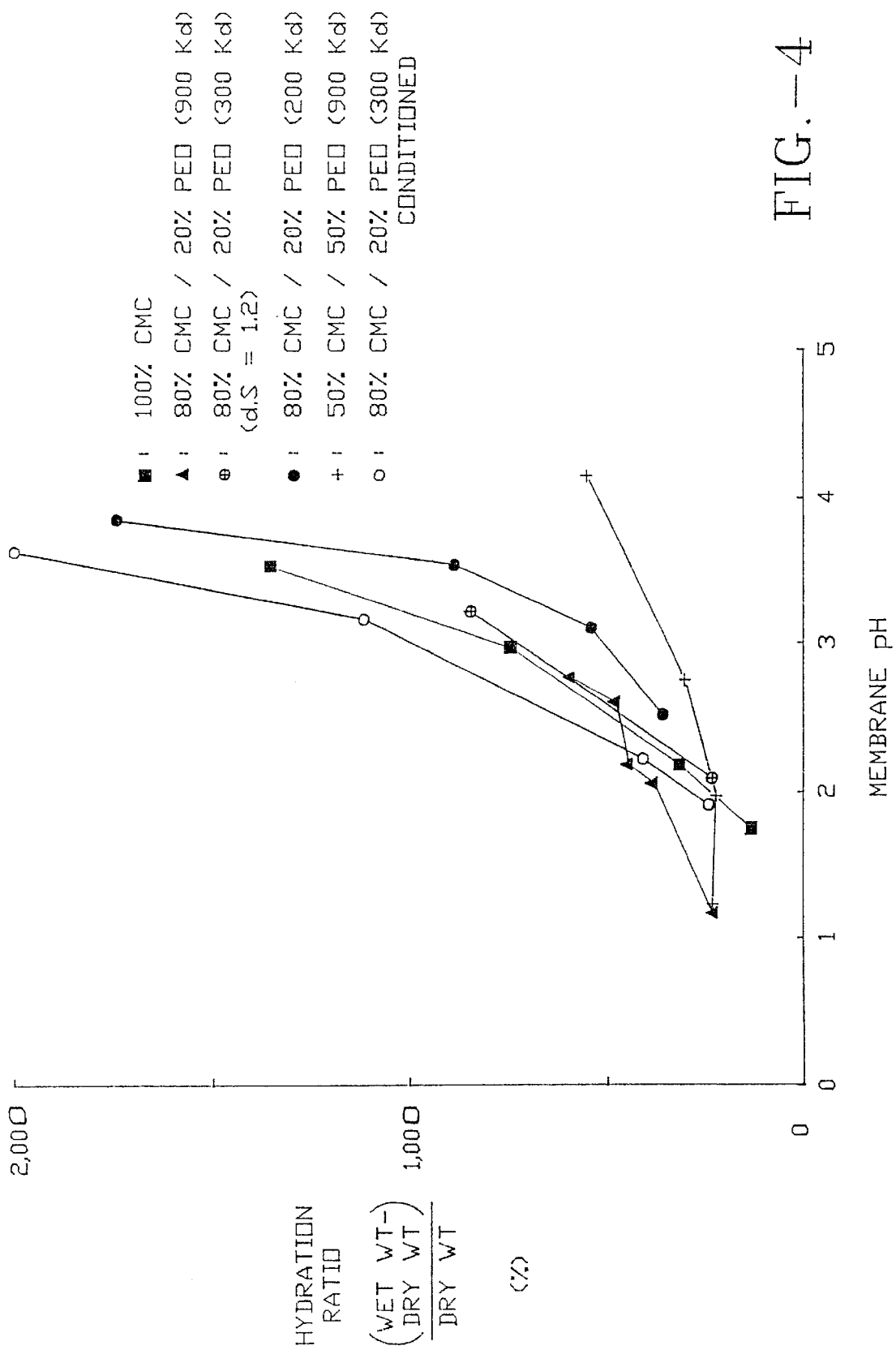
FIG. 4 shows the hydration or swelling of CMC/PEO membranes in phosphate buffered saline (PBS) solution with a pH of 7.4 at room temperature.

The membranes of the present invention rapidly hydrate in PBS solution (FIG. 3). This behavior mimics that of membranes placed on moist tissues during surgery. The hydration of the membranes increases both the thickness of the barrier and its flexibility, thus permitting it to conform to the shape of the tissues to be separated during the period during which adhesions could form. The preferred hydration ratios (% increase in mass due to water absorption) for optimum adhesion prevention are 500%–4000%, more preferred ratios are between 700%–3000%, and the most preferred hydration ratio for alleviating adhesions is approximately 2000% (FIG. 4).

In addition to decreasing the pH of the association complex, increased intermacromolecular association is achieved using CPSs with increased degree of carboxyl substitution. By increasing the density of protonatable carboxyl residues on the CPS, there is increasing likelihood of hydrogen bond formation even at a relatively high pH. The degree of substitution must be greater than 0, i.e., there must be some carboxyl residues available for hydrogen bond formation. However, the upper limit is theoretically 3 for cellulose derivatives, wherein for each mole of the saccharide, 3 moles of carboxyl residues may exist. Thus, in the broadest application of the invention, the d.s. is greater than 0 and up to and including 3. Preferably, the d.s. is between 0.3 and 2. CPS with d.s. between 0.5 and 1.7 work well, and CPSs with a d.s. of about 0.65–1.45 work well and are commercially available.

The complexes of the instant invention are intended to have a finite residence time in the body. Once placed at a surgical site, the dried membranes hydrate rapidly, turning into a gel-like sheet and are designed to serve as a barrier for a limited time period. Once healing has substantially taken place, the anti-adhesion barrier naturally disintegrates, and the components are cleared from the body. The time taken to clear the body should preferably be no more than 29 days because of increased regulation by the Food and Drug Administration of devices intended to remain within the body for more than 30 days.

Figure 5:
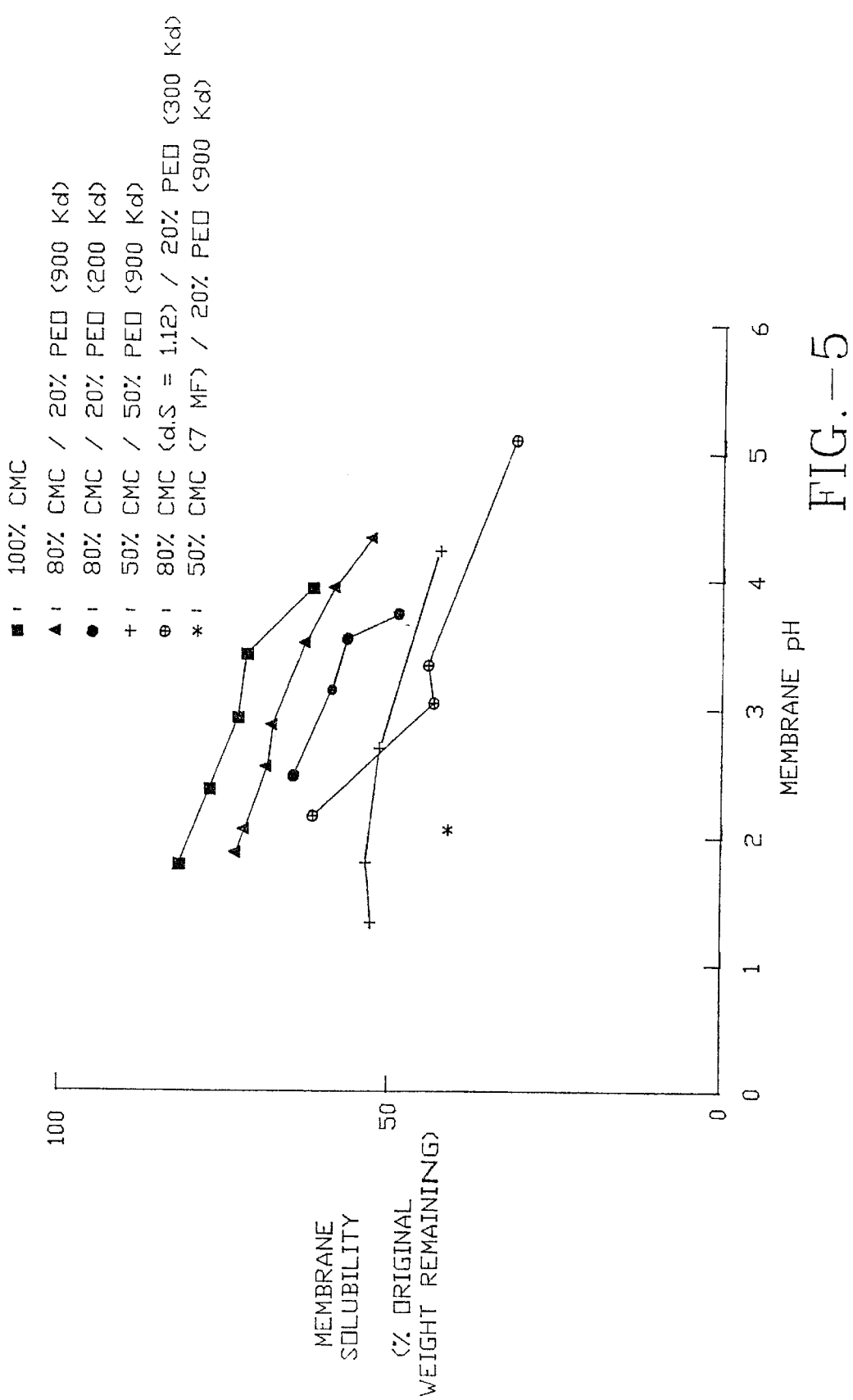
FIG. 5 shows solubility in PBS of membranes of different composition and pH.

The mechanisms for bioresorption of CMC/PEO complexes are not well understood. However, an early step in the process of bioresorption is solubilization of the network of CMC and PEO. Thus, increasing the solubility of the complex increases the ease of clearing the components from the tissue (FIG. 5). When soluble, CMC and PEO can diffuse into the circulation and be carried to the liver and kidneys, where they may be metabolized or otherwise eliminated from the body. Additionally, enzymatic action can degrade carbohydrates. It is possible that enzymes contained in neutrophils and other inflammatory cells may degrade the polymer networks and thereby increase the rate of elimination of the components from the body.

The degradation and rate of solubilization and disruption of the membrane is manipulated by careful adjustment of the pH during formation of the association complexes, by varying the CPS/PE ratio, and by selecting the appropriate degree of substitution of the CPS and molecular weights of the PE and CPS. Decreasing the molecular weight of CPS increases its solubility. (Kulicke et al., *Polymer* 37(13):2723–2731 (1996). The strength of the membrane can be tailored to the surgical application. For example, certain surgical applications (e.g., spine or tendon) may require a stronger, more durable membrane than others (such as intraperitoneal applications). Manipulation of the above-mentioned experimental variables allows the manufacture and use of products with variable residence times in the body.

Figure 6:
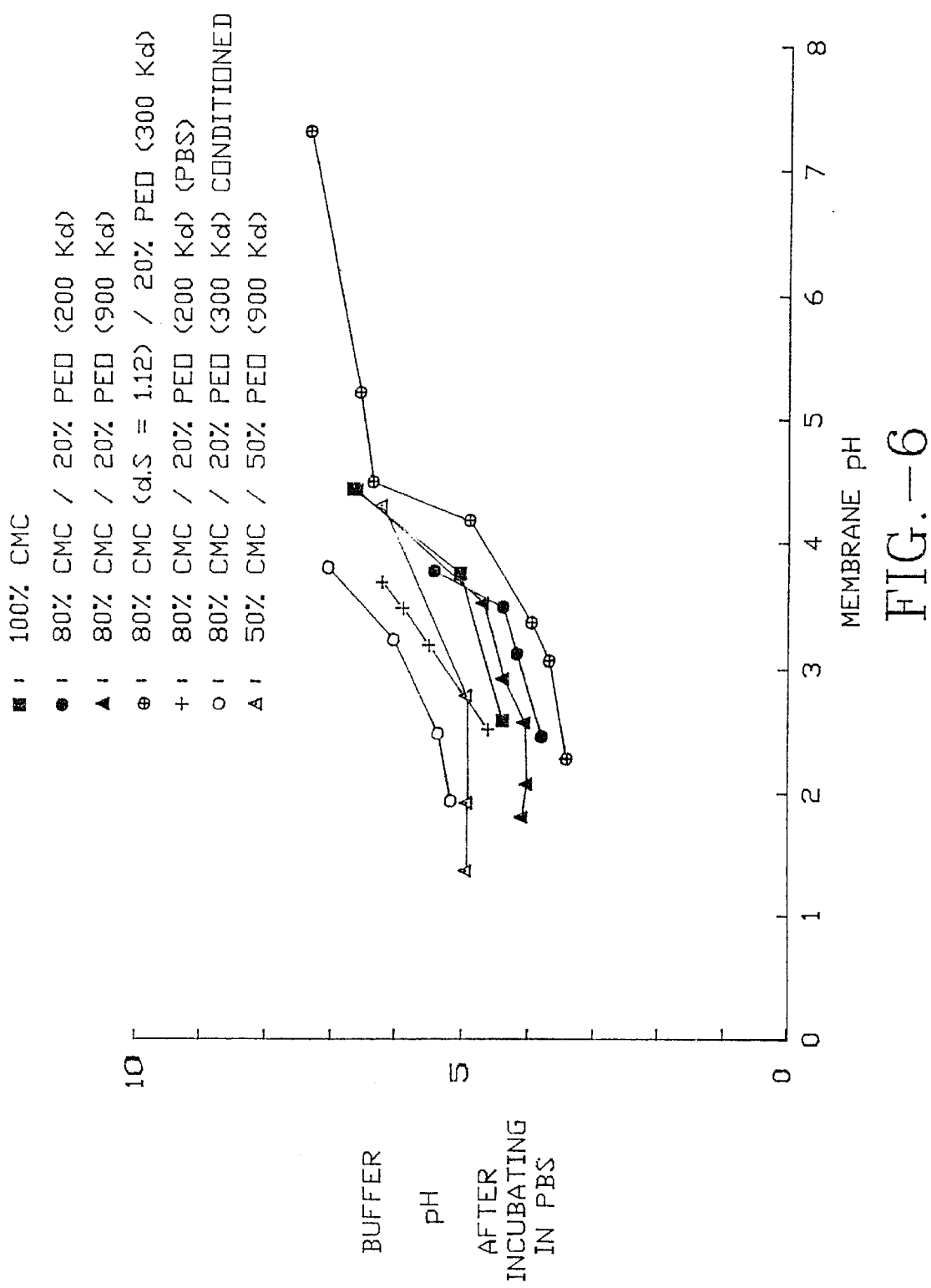
FIG. 6 shows results of studies of the acidification of PBS solutions by CMC/PEO membranes.

Biocompatability of the complex of the present invention is a function of its acidity. A highly acidic complex contributes a relatively larger total acid load to a tissue than does a more neutral complex. Additionally, the more rapidly hydrogen ions dissociate from a complex, the more rapidly physiological mechanisms must compensate for the acid load by buffering, dilution and other clearance mechanisms. To mimic the rate and total amount of acid given up by a membrane in vivo, membranes are placed in PBS solutions and the degree of acidification of the PBS is measured. In addition to membrane pH, membrane composition also influences the acid load delivered to the body. FIG. 6 and Tables 3 and 6 show the results of studies designed to mimic the delivery of acid by membranes to tissues.

After their manufacture, membranes may be modified to suit the particular needs of the user. For example, relatively bioresorbable membranes may be made more insoluble by treating them with solutions containing an acid, exemplified, but not limited to hydrochloric, sulfuric, phosphoric, acetic, or nitric acid, the "acidic" method.

Conversely, a relatively non-resorbable acidic membrane may be made more bioresorbable and bioadhesive by conditioning it with alkali such as ammonia (the "alkaline" method), or with a buffered solutions such as phosphate buffer (PB) or phosphate buffered saline (PBS; the "buffer" methods). A 10 mM solution of PBS at a pH of 7.4 is preferred, due to the biocompatability of phosphate buffers. Moreover, the pH of a membrane may be buffered without eliminating the advantages of membranes made at lower pH. Thus, an originally acid membrane will hydrate slowly and have a relatively long residence time even if its pH is raised by alkali or buffer treatment.

Table 7 shows the effects of ammonia treatment on properties of CMC/PEO membranes. A highly acidic original membrane (pH 2.03) acidified a PBS buffer solution originally at a pH of 7.40 by lowering its pH to 4.33. After soaking this membrane in PBS solution, it hydrated to over 2.5 times its original dry weight and after 4 days in PBS, this membrane lost approximately 29% of its original mass. In an identical membrane, incubation for 1 min in a 0.5N ammonia solution substantially neutralized the membrane so that it released few hydrogen ions into the buffer solution, and the pH of the PBS solution remained nearly neutral (pH 7.29).

Table 8 shows the effects of phosphate-buffer treatment on properties of CMC/PEO membranes. Membranes treated with 50 mM phosphate buffer solution for progressively longer time periods had increasingly neutral pH as judged by their decreased release of acid into a PBS solution. Similarly, PBS (10 mM phosphate buffer) neutralized the acid in membranes (Table 9). Therefore, membranes can be made which are physiologically compatible with tissues, yet because they are made at an acidic original pH which creates an association complex, the membranes retain the desired properties of the original complex.

Additionally, multi-layered membranes may be made, for example, to incorporate a low pH inner membrane, surrounded by an outer membrane made with a higher pH. This composition permits the introduction of a membrane with long-term stability and low rate of bioresorbability of the inner membrane while minimizing adverse effects of low pH membranes, such as tissue damage and the stimulation of inflammatory responses. Moreover, the high pH outer portion is more bioadhesive than low pH membranes, ensuring that such a membrane remains at the site more securely.

Multilayered membranes may also be made which include as one layer, a pure CPS or PE membrane. Such a membrane could have the flexibility, antiadhesion, and solubility properties of the side which is a mixture of CPS and PE, and have the property of the pure material on the other. For example, bioadhesiveness is a property of CPS, and a pure CPS side would have the highest degree of bioadhesiveness. Alternatively, a pure PE membrane would have the most highly antithrombogenic properties. Thus, a membrane can be made which incorporates the desired properties of each component.

Membranes can be made which incorporate drugs to be delivered to the surgical site. Incorporation of drugs into membranes is described in Schiraldi et al., U.S. Pat. No. 4,713,243. The incorporation may be at either the manufacturing stage or added later during membrane conditioning prior to insertion. Drugs which may inhibit adhesion formation include antithrombogenic agents such as heparin or tissue plasminogen activator, drugs which are anti-inflammatory, such as aspirin, ibuprofen, ketoprofen, or other, nonsteroidal anti-inflammatory drugs. Furthermore, hormones, chemotactic factors, analgesics or anesthetics may be added to the membrane, either during manufacture or during conditioning. Any drug or other agent which is compatible with the membrane components and membrane manufacture may be used with the present invention.

The types of surgery in which the compositions of the instant invention may be used is not limited. Examples of surgical procedures include abdominal, ophthalmic, orthopedic, gastrointestinal, thoracic, cranial, cardiovascular, gynecological, arthroscopic, urological, plastic, or musculoskeletal.

Between 67% and 93% of all laparotomies and laparoscopies result in adhesion formation. Specific abdominal procedures include surgeries of the intestines, appendix, cholecystectomy, hernial repair, lysis of peritoneal adhesions, kidney, bladder, urethra, and prostate.

Gynecological procedures include surgeries to treat infertility due to bilateral tubal disease with adhesion attached to ovaries, fallopian tubes and fimbriae. Such surgeries including salingostomy, salpingolysis and ovariolysis, Moreover, gynecological surgeries include removal of endometriosis, preventing de-novo adhesion formation, treatment of ectopic pregnancy, myomectomy of uterus or fundus, and hysterectomy.

Musculoskeletal surgeries include lumbar laminectomry, lumbar discectomy, flexor tendon surgery, spinal fusion and joint replacement or repair.

Thoracic surgeries which involve sternectomy can be hazardous after primary surgery because of adhesion formation between the heart or aorta and sternum. Thoracic surgeries include bypass anastomosis, and heart valve replacement.

Because many cranial surgical procedures require more than one procedure, adhesions involving the skull, dura and cortex can complicate the secondary procedures.

Ocular surgical uses include strabismus surgery, glaucoma filtering surgery, and lacrimal drainage system procedures.

General Methods For Testing And Evaluating Antiadhesion Membranes

Hydration Ratio of Membranes

To determine the rate of hydration and the hydration ratio of membranes, pieces of dry membranes, preferably 160 mg, were placed singly in a glass vial and 20 ml phosphate buffered saline solution (PBS, 10 mM, pH 7.4, Sigma Chemical Company, St. Louis, Mo.) was added. The membranes hydrate, creating soft sheets of hydrogel. After a certain time period (typically 1 hr to 5 days), each of the hydrated membranes was carefully removed from the test vial and placed in a polystyrene petri dish. Excess water was removed using a disposable pipette and by blotting the membrane with tissue paper. Each membrane was then weighed and the hydration ratio (% H) was determined according to the following formula:

$$\% H = \frac{(\text{wet mass} - \text{dry mass})}{\text{dry mass}} \times 100\%.$$

Solubility of CPS/PE Membranes

To determine the solubility of CPS/PE membranes, we measured the relative solubility in water and the aqueous stability of the membranes as a function of their chemical compositions. Membrane solubility in water correlates with the resorption time of the membranes in-vivo.

Typically, the test is performed in conjunction with the hydration measurements outlined above. However, the membranes take up salt during the hydration test due to exposure to PBS. This added salt results in an artifactually high dry weight. Therefore, after determining the hydration ratio, we soaked the membranes in deionized water (30 ml for 30 min.) to remove the salt incorporated in the polymer network. The water was decanted and a fresh 30 ml aliquot of deionized water was added. The membranes were allowed to soak for another 30 min., were taken out of the petri dishes, were blotted dry and were placed in a gravity convection oven at 50° C. to dry.

The drying time was dependent on the amount of water absorbed by the membrane. Highly hydrated, gel-like membranes took up to 24 hours to dry whereas partially hydrated membranes took as little as a few hours to dry. After the membranes lost the excess water, the membranes were allowed to equilibrate at room temperature for 1–2 hours before weighing them. The weight measurements were repeated until a constant weight was obtained. Typically, some rehydration of the membrane took place during this period due to adsorption of moisture from the air.

After the desalinization process described above, the membranes were placed in petri dishes containing 30 ml deionized water to hydrate for periods of from 20 minutes to 5 days. Preliminary studies showed that membranes at pH within the range of 6 and below did not disintegrate during the 1 hr desalinization period.

The solubility (S) of membranes was calculated using the following formula:

$$\% S = \frac{(\text{dry mass before soaking} - \text{dry mass after soaking})}{\text{dry mass before PBS soaking}} \times 100\%.$$

The dry mass before soaking is the mass after desalinization, and the dry mass after soaking is the mass after the hydration period in water.

Determination of Acid Load Delivered by Membranes

This test was performed in conjunction with the hydration and solubility tests described above. The test gives an indication of the acid load which the membrane could deliver to a tissue when placed implanted in an animal or human subject. After manufacture, the membranes were placed in a PBS solution, the complex released protons in a time-dependent way resulting in a measurable decrease in pH of the PBS solution.

The acid load test was performed using a Model 40 pH meter (Beckman Instruments, Fullerton, Calif.). 160 mg of dry membrane was placed in a glass vial and 20 ml PBS was added. The initial pH of the PBS solution was 7.40; the pH of this solution was gradually decreased as the polymers in the membrane partly dissolved thereby exposing more protonated carboxylic residues. In highly hydrated membranes (pH 4–7) this process was accelerated as the polymer chains were pulled apart by the hydrostatic forces generated during the hydrating process.

EXAMPLES

In the following examples, carboxypolysaccharide/polyether membranes are described for CMC as an exemplary carboxypolysaccharide, and PEO is the exemplary polyether. It is understood that association complexes of other carboxypolysaccharides and polyethers can be made and used in the same ways. Thus, the invention is not limited to these Examples, but can be practiced in any equivalent fashion without departing from the invention.

Example 1

Neutral CMC/PEO Membranes

Type 7HF PH (MW approximately 700 kd; lot FP 10 12404) carboxymethylcellulose sodium (CMC) was obtained from the Aqualon Division of Hercules (Wilmington, Del.). PEO with a MW of approximately 900 kd was obtained from Union Carbide (Polyox WSR-1105 NF, lot D 061, Danbury Conn.); PEO with a MW of approximately 1000 kd was obtained from RITA Corporation (PEO-3, lot 0360401, Woodstock, Ill.).

A membrane with a composition of 65% CMC and 35% PEO was made as follows: 6.5 g of CMC and 3.5 g of PEO was dry blended in a weighing dish. A Model 850 laboratory mixer (Arrow Engineering, Pa.) was used to stir 500 ml of deionized water into a vortex at approximately 750 RPM. The dry blend of CMC and PEO was gradually dispersed to the stirred water over a time period of 2 min. As the viscosity of the polymer solution increased as the polymers dissolved, the stirring rate was gradually decreased. After approximately 15 min., the stirring rate was set at between 60–120 RPM and the stirring was continued for approximately 5 h to obtain a homogeneous solution containing 2% total polymer concentration (wt/wt) without any visible clumps.

Instead of pre-blending the CMC and PEO, an alternative way of formulating the casting solution for the membranes is to individually dissolve the polymers. The anionic polymer, CMC, can be then acidified by adding the appropriate amount of HCl. For example, a 500 ml batch of 2% CMC made by dissolving 10.0 g of CMC 7HF in 500 ml deionized water was acidified to a pH of 2.6 by adding 2700 µl concentrated HCl ("solution A"). Separately, a batch of 2% PEO was made (w/v 900,000 MW, "solution B"). Solutions A and B are then thoroughly mixed in a specific ratio using the laboratory stirrer of Example 1 at 60 RPM. The total polymer concentration was kept at 2% (w/v), as in Examples 1–2.

Membranes were cast from solutions by pouring 20 g of solution into 100×15 mm circular polystyrene petri dishes (Fisher Scientific, Santa Clara, Calif. The petri dishes were placed in a laboratory gravity convection oven set at 40°–45° C., and were allowed to dry overnight at 760 Torr. The resulting membranes were carefully removed from the polystyrene surface by using an Exacto knife.

For larger membranes, 243×243×18 mm polystyrene dishes (Fisher Scientific) were used. Using the same weight to surface area ratio as for the circular membranes (in this case, 220 g of casting solution was used), resulted in a membrane which had a dry weight of approximately 4.5 g. The membrane appeared homogeneous, smooth, and pliable. Placing 160 mg of this membrane in 20 ml of a PBS solution (pH 7.4) did not change the pH of the solution. The dry tensile strength and % elongation at break were slightly higher than corresponding membranes which were made from an acidified casting solution (Table 2). When placed in deionized water or PBS, the membrane exhibited excessive swelling and lost its sheet structure rapidly (within 10 min.) to form a gel-like substance which eventually homogeneously dispersed into a polymer solution.

Example 2

Moderately Acidified CMC/PEO Membranes And Hydrogels

The procedure for making acidified membranes in the intermediate pH region (2.5<pH<7) initially follows the procedure outlined in Example 1. The neutral blended polymer solution containing the polymers specified in Example 1 is acidified by adding concentrated hydrochloric acid (HCl, 37.9%, Fisher Scientific, Santa Clara, Calif.) while stirring the polymer solution at 60–120 RPM for 1 hour. Initially, a white precipitate forms in the solution; the precipitate gradually disappears and a stable solution is formed. Typically, a 2% total polymer concentration was found useful to achieve the desired viscosity for stable casting solutions. Higher polymer concentrations resulted in polymer solutions which were too viscous and too difficult to pour. Lower polymer concentrations required more casting solution for the same membrane weight which greatly increased drying time for equivalent membranes. In the 500 ml 65% CMC/35% PEO polymer blend of Example 1, 1500 µl of concentrated HCl is needed to achieve a pH of 3.1 in the casting solution. The viscosity of the starting polymer solution dropped by at least 50% by this acidification process.

The titration curves for various polymer blends (as well as 100% CMC and 100% PEO) are shown in FIG. 2. FIG. 2 shows the amount of HCl needed to make casting solutions of desired pHs depending upon the composition of the CMC/PEO mixture. Membranes made of 100% CMC (■) require more acid than do other compositions to become acidified to the same degree. Increasing the concentration of PEO (decreasing the concentration of CMC) decreases the amount of acid necessary to acidify a casting solution to a desired point. Increasing the PEO concentration to 20% has a small effect, regardless of whether the molecular weight of the PEO is 200 k (●) or 1000 kd (▲). Increasing the PEO concentration to 40% (+) or to 100% (□) further decreases the amount of acid needed to achieve a desired casting solution pH.

Viscosity of Hydrogels

Because the antiadhesion properties of a hydrogel are dependent upon its viscosity, we determined the relationship between casting solution pH and the viscosity of the hydrogel. We determined the viscosity of PCS/PE solutions at 22° C. using a Brookfield™ viscometer. Using methods published in the brochure *Cellulose Gum*, Hercules, Inc., Wilmington, Del., (1986), page 28. Briefly, the composition of the solution to be tested is selected, and by referring to Table XI on page 29 of Cellulose Gum, the spindle number and spindle revolution speed is selected. Viscosity measurements are made within 2 hr after stirring the solution. After placing the spindle in contact with the solution, and permitting the spindle to rotate for 3 minutes, the viscosity measurement is read directly in centipoise on a Brookfield Digital Viscometer (Model DV-II). We studied 65% CMC/35% PEO solutions made with 7HF PH CMC and 1000 kd PEO (RITA) at a pH of 7.5. Another 65% CMC/35% PEO solution was made at a pH of 3.1.

TABLE 1

Effect of Casting Solution pH On Hydrogel Viscosity

| RPM | Viscosity @ pH 7.5, 22° C. (centipoise) | Viscosity @ pH 3.1, 22° C. (centipoise) |
|---|---|---|
| 0.5 | 38,000 | 13,000 |
| 1.0 | 31,000 | 12,000 |
| 2.0 | 23,200 | 10,400 |

TABLE 1-continued

Effect of Casting Solution pH On Hydrogel Viscosity

| RPM | Viscosity @ pH 7.5, 22° C. (centipoise) | Viscosity @ pH 3.1, 22° C. (centipoise) |
|---|---|---|
| 5.0 | 19,400 | 8,800 |
| 10 | 15,500 | 7,300 |

Table 1 shows the change in viscosity due to acidificiation of casting solutions. Reducing the pH from 7.5 to 3.1 decreased the viscosity of the casting solution by more than half. Because the viscosity of a hydrogel is related to its ability to prevent adhesions, possibly due to its ability to remain in one site for a longer time period, gels of higher pH have greater anti-adhesion properties. Further, it is also possible to characterize casting solutions by their viscosity as well as their pH. Thus, for situations in which the measurement of pH is not be as easy or reliable, measurements of viscosity are preferred. To make membranes, the acidified casting solutions containing the weakly H-bonded intermolecular PEO-CMC complex were next poured into polystyrene dishes and dried out in a similar way as described in Example 1. After drying, physical properties were determined.

Physical Properties of CMC/PEO Membranes

Tensile strength and elongation of membranes are measured for pieces of membrane in the shape of a "dog bone," with a narrow point being 12.7 mm in width. The membranes are then mounted in an Instron™ tester equipped with a one ton load cell. The crosshead speed is set at 5.0 mm/min. We measured membrane thickness, tensile strength, and elasticity (% elongation of the membrane at the break point). Results are reported for those samples that had failure in the desired test region. Those samples that either failed at the radius of the sample or in the grips were considered improper tests and results of those tests were discarded.

TABLE 2

Physical Properties of CMC/PEO Membranes

| Membrane Composition | Thickness (mm) | Tensile Strength (psi) | % Elongation at Break Point |
|---|---|---|---|
| 65% CMC/35% PEO (1000 kd), pH 3.1 | 0.081 | 6017 | 4.17 |
|  | 0.076 | 5527 | 4.47 |
|  | 0.076 | 5956 | 5.07 |
| 65% CMC/35% PEO (1000 kd), pH 7.5 | 0.071 | 10,568 | 6.69 |
|  | 0.069 | 10,638 | 6.61 |
| 80% CMC/20% PEO (5000 kd), pH 3.1 | 0.084 | 3763 | 3.20 |

The membranes are all less than 0.1 mm thick. Decreasing the pH of the membrane from neutral decreases the tensile strength, and decreases the elasticity (% elongation) at the break point. Similarly, decreasing the PEO concentration decreases the tensile strength and elasticity of the membranes.

Hydration of CMC/PEO Membranes in PBS

To evaluate the bioadhesive properties of membranes, we determined the rate and extent of hydration properties of CMC/PEO membranes according to the methods described above.

FIG. 3 shows the time course of hydration of CMC/PEO membranes of the present invention. A membrane made of 80% CMC/20% PEO (m.w. 900 kd) at a pH of 4.31 rapidly hydrated (●). After 2 h in PBS, its hydration ratio (wet wt.-dry wt)/dry wt; % swelling) increased to more than 6000%. After, 5 h in PBS, this membrane's hydration ratio was nearly 8000%. This highly hydrated membrane lost its cohesiveness and substantially disintegrated thereafter. Reducing the membrane pH to 3.83 and below resulted in membranes which hydrated nearly to their equilibrium points within 2 hrs. and maintained their degree of hydration and cohesiveness for at least 40 hrs. The degree of hydration was dependent upon the membrane pH with the least acidic membranes being capable of swelling to a higher degree. At a pH of 3.83 (▲), the membrane had a hydration ratio of nearly 6000%, whereas at a pH of 2.0 (□), the hydration ratio was less than 300%. Within the range of pH from 3.2 to 4.3, the degree of hydration is very sensitive to the pH.

FIG. 4 shows a summary of another study of the effect of membrane composition and pH on the hydration of CMC/PEO membranes. Hydration was measured after at least 6 hrs in PBS-, a time after which the degree of hydration had nearly reached equilibrium for each membrane (see FIG. 3). For each of the compositions studied, increasing the membrane pH increased the hydration of the membrane. Membranes of 100% CMC (■) increased their hydration ratios from approximately 100% at a membrane pH of 1.7 to over 1300% at a membrane pH of 3.4. For membranes made of 80% CMC/20% PEO, the molecular weight of the PEO had a slight effect on hydration. Membranes made with 900 kd PEO (▲), hydrated slightly more at a given pH than membranes made with 200 kd PEO (●). Furthermore, membranes made with CMC of a higher degree of substition (d.s.=1.2; ⊕) hydrated similarly to those of 100% CMC with a degree of substitution of 0.84 (■). Finally, membranes that were made with 50% CMC/50% PEO (900 kd) hydrated less than any of the other membranes, except at low membrane pH (<2.5).

Solubility of CMC/PEO Membranes

Because the biodegradation of CPS/PE polymers is related to solubility, we measured the solubility of membranes after at least 4 days in PBS according to methods described above. FIG. 5 shows the effects of membrane pH and composition on the solubility of membranes in PBS solution. Membranes were made of different CMC/PEO compositions and at different membrane pHs. For all membranes, as the membrane pH increased, the solubility in PBS increased. Membranes of 100% CMC (■) were the least soluble. Membranes containing PEO were more soluble, with membranes made of 900 kd PEO (▲) being less soluble than membranes of 200 kd PEO (●). Further increasing the percentage of PEO to 50% (+) further increased membrane solubility. Decreasing the molecular weight of the CMC (7MF;*) increased the solubility. Additionally, increasing the degree of substitution of the CMC from 0.84 to 1.12 (⊕) resulted in even more soluble membranes. Also, with the higher degree of substitution, there was a larger effect of pH on membrane solubility. For the other membranes, the effect of increasing pH appeared to be of similar magnitude regardless of the composition of the membrane. Thus, the slopes of the lines were similar. These results indicate that regardless of membrane composition, the solubility of membranes can be increased by increasing the membrane pH. Moreover, because bioresorption requires solubilization, more highly soluble membranes will be cleared from the body more rapidly than less soluble membranes.

Biocompatability Of CMC/PEO Membranes

Because biocompatability is related to the acid load delivered to a tissue, we determined the acid load delivered by CMC/PEO membranes to a PBS solution as described above as a suitable in-vitro model. We first determined the time course of acidification of PBS solutions exposed to different compositions of CMC/PEO membranes.

TABLE 3

Time Course Of Acidification Of PBS By CMC/PEO Membranes

| Membrane Composition | Casting Solution pH | Time in PBS Solution (hr) | | | | 45h PBS pH Change |
|---|---|---|---|---|---|---|
| | | 1 | 3.5 | 21 | 45 | |
| 80% CMC/ 20% PEO (900 kd) | 1.85 | 6.26 | 5.62 | 4.78 | 4.64 | 2.76 |
| | 3.17 | 6.53 | 5.71 | 5.61 | 5.65 | 1.75 |
| 50% CMC/ 50% PEO (900 kd) | 1.77 | 6.60 | 6.12 | 5.62 | 5.42 | 1.98 |
| | 2.71 | 6.47 | 6.13 | 6.01 | 5.98 | 1.42 |
| 80% CMC/ 20% PEO (8 kd) | 1.82 | 3.71 | 3.39 | 3.52 | 3.45 | 3.95 |

Table 3 shows the kinetics of acidification of a PBS solution by CMC/PEO membranes of the instant invention. When added to a PBS solution, membranes released acid into the solution, thereby lowering the solution pH. This process occured slowly, with a reduction in solution pH of approximately 1 pH unit in the first hour for membranes including those combining high molecular weight PEO. This is true for membranes cast from low pH polymer solutions as well as those cast from higher pH polymer solutions. The remaining reduction in pH occurred over the next 20 hrs, at which time the solution pH remained approximately constant. By 45 hrs in the PBS solution, the pHs have decreased to below 6.0.

Additionally, as the molecular weight of the PEO decreased, the solution pH decreased more rapidly and to a higher degree than membranes made of high molecular weight PEO. This finding might be due to an ability of higher molecular weight PEOs to shield the acidic carboxyl residues of the CMC, thereby decreasing the dissociation of carboxyl hydrogen ions.

These results suggest that high molecular weight PEO acts to slow the delivery of acid to tissues, and thus, protects them from excessive acidification. Moreover, as protons are released in vivo, they will be diluted in the extracellular spaces, buffered by physiological buffers, and ultimately cleared from the tissue by the lymphatic and circulatory systems. Over the relatively long time during which protons are released, the physiological dilution, buffering, and clearance mechanisms will remove the acid load, keeping the pH at the tissue within acceptable ranges. Thus, these membranes are suitable for implantation in vivo without causing excessive tissue disruption due to a large acid load being delivered.

FIG. 6 shows the results of studies in which the pH of the PBS solution varies as a function of the membrane pH and composition of the membrane. Membranes were placed in PBS solution for 4–5 days, times at which the acidification had reached equilibrium (Table 3). The membrane composition which resulted in the least acidification were the pre-conditioned 80/20/300 k membranes (○). These membranes were made as described above, except for an additional step of soaking the membranes in PBS and then re-drying them (see Examples 7–9). The 80/20/200 k membranes cast in PBS (+) delivered the next lowest acid load, and the 50/50 CMC/PEO (900 k) series of membranes (Δ) delivered the third lowest acid load to the PBS solution. Membranes made of 100% CMC: (■), 80/20/200 k (●), and the 80/20/900 k (▲) delivered progressively more acid to the PBS, and the 80/20/300 k series of membranes made with CMC with a degree of substitution of 1.12 delivered the most acid to the PBS solution.

FIG. 6 also shows that conditioning membranes by soaking them in PBS decreased the acid load delivered to the PBS solution. For example, a pre-conditioned membrane cast at an original pH of 3.4 reduced the pH of the PBS solution only to 7.0 from 7.4. Thus, for those applications in which a long lasting membrane is needed, but one which will cause the least acidification, preconditioning of an acidic membrane in PBS is desirable.

Example 3

Membranes With Different PEO/CMC Ratios

A 500 ml batch of a 80/20 CMC/PEO membrane was obtained by dissolving 8.0 g CMC and 2.0 g PEO in 500 mL deionized water (source of CMC and PEO, and solution processes were as in Example 1). While stirring at low speed (60 RPM), 200 g of this polymer solution was acidified with 1500 μl of 5 N HCl (LabChem, Pittsburgh, Pa.), resulting in an equilibrium pH of 3.17. The acidified polymer solution was next poured into polystyrene dishes and dried out in a similar way as described in Example 1. By changing the relative amounts of CMC and PEO, membranes with different compositions were obtained. 100% CMC membranes were more brittle and less flexible than PEO-containing membranes. For our purposes, membranes which contain more than 70% PEO are generally not preferable as these membranes were unstable in an aqueous environment.

TABLE 4

Viscosity Of Solutions with Different CMC/PEO Ratios (cps, @ Spindle #6, 20° C.)

| Membrane Composition (1000 kd PEO) (% CMC/% PEO; pH) | Spindle RPM | | | | |
|---|---|---|---|---|---|
| | 0.5 | 1.0 | 2.5 | 5.0 | 10.0 |
| 25/75 | | | | | |
| 4.0 | 8000 | 7000 | 4800 | 4400 | 3700 |
| 2.6 | 3200 | 3000 | 2800 | 2400 | 2000 |
| 33/66 | | | | | |
| 4.0 | 8000 | 7000 | 6800 | 6200 | 5100 |
| 2.6 | — | 3000 | 3200 | 2800 | 2500 |
| 50/50 | | | | | |
| 4.0 | 16,000 | 15,000 | 12,800 | 10,600 | 8400 |
| 2.6 | 4000 | 5000 | 4800 | 4200 | 3500 |
| 66/33 | | | | | |
| 4.0 | 28,000 | 25,000 | 20,400 | 16,000 | 12,300 |
| 2.6 | 8000 | 7000 | 6400 | 5800 | 4900 |
| 100% CMC | | | | | |
| 4.0 | 72,000 | 61,000 | 42,800 | 31,600 | 28,700 |
| 2.6 | 88,000 | 67,000 | 42,400 | 29,400 | 20,400 |
| 100% PEO (900 kd) 2.6 | 480 | 300 | 280 | 290 | 290 |

Table 4 shows the effect of CMC/PEO ratio on solution viscosity. Membranes were made with different percentages of PEO (m.w.: 1,000,000) at two different pHs. Solutions containing higher proportions of CMC were more viscous than solutions containing less CMC. Furthermore, the less acidic solutions had a higher viscosity than solutions with more acidity. This relationship held for all solutions except for the 100% CMC solution. At a pH of 2.6, the viscosity was slightly higher than at a pH of 4.0. This was possibly due to the association between CMC molecules at lower pH.

Larger than expected viscosity decreases were obtained when the two solutions were mixed. For example, an 85% loss in viscosity was achieved when solutions A (pH 2.6) and B were mixed in a 50/50 ratio. At a spindle RPM of 2.5, the starting 2% CMC concentration (w/v), pH 2.6 solution had a viscosity of 42,400 cps, the 2% PEO solution had a viscosity of 280 cps. Thus, if viscosity of a mixture is the average of the viscosities of the components, we would expect that a 50/50 CMC/PEO solution would have a viscosity of (42400+280)2=21300 cps (approximately a 50% viscosity decrease from that of CMC alone). However, the actual CMC/PEO (50/50) solutions had a viscosity of only 4,800 CPS. A similar, more than expected decrease in viscosity was reported by Ohno et al. (*Makromol Chem., Rapid Commun.* 2, 511–515, 1981) for PEO blended with dextran and inulin.

Further evidence for intermolecular complexation between CMC and PEO is shown by comparing the relative decreases in viscosity caused by acidification for the 100% CMC and CMC/PEO mixtures. Table 4 shows at 2.5 rpm, the viscosity of CMC solution remained essentially unchanged when the pH was decreased from 4.0 to 2.6. However, for mixtures of CMC/PEO, the acifidiation caused a large decrease in viscosity. The decreases were by 69%, 63%, 53%, and 42% for mixtures of CMC/PEO of 66%/33%, 50%/50%, 33%/66%, and 25%/75%, respectively.

Thus, there is an intermolecular association between CMC and PEO, which, we theorize, results in PEO molecules becoming interspersed between CMC molecules, thereby preventing intermolecular bonding between the CMC molecules. Such a theory could account for the observations, but we do not intend to limit the present invention to any single theory of molecular interaction. Other theories may account for the observations.

Next, after manufacturing membranes with different CMC/PEO ratios we studied their hydration, acid load, and solubility properties using methods described above.

TABLE 5

Effect of CMC/PEO Ratio on Hydration, Acid Load and Solubility

| Membrane Composition (% CMC 7HF/ % PEO 900 kd) | Membrane pH | Hydration Ratio (%) | Acid Load (PBS pH) | Solubility (% Mass Loss) |
|---|---|---|---|---|
| 100% CMC | 2.52 | 1145 | 3.46 | 9.7 |
| 66/33 | 2.87 | 2477 | 3.80 | 30 |
| 50/50 | 2.94 | 3077 | 4.58 | 34 |
| 33/66 | 2.98 | (dissolved) | 5.88 | (dissolved) |

Table 5 shows the effect of increasing the PEO concentration in CMC-PEO membranes on the % water uptake, acidity, and mass loss. Increasing the PEO content of membranes increases the hydration ratio and solubility and decreases the acid load delivered to PBS. These results indicate that as the total amount of CMC in the membrane decreases, the acid load decreases.

The effect of a different CMC/PEO ratios is further demonstrated in FIG. 5 (solubility vs. membrane pH), and FIG. 6 (membrane acidity vs. PBS solution pH).

Example 4

Membranes Of Different Molecular Weight PEO

Membranes of PEO's of different molecular weight were made by mixing 2% (w/v) PEO solutions with 2% (w/v) solutions of CMC (type 7HF PH (lot FP 10 12404) obtained from the Aqualon Division of Hercules (Wilmington, Del.). PEO's with a molecular weight of 8000 (8K) was obtained as Polyglycol E8000NF from Dow Chemical, Midlands, Mich. The PEO's with molecular weights of 300,000 (300K), 900,000 (900K), and 5,000,000 (5M) were all from Union Carbide. 2% (w/v) solutions of PEO were made by dissolving 6.0 g of PEO in 300 ml deionized water according to the methods used in Example 1. The CMC stock solution was similarly made by dissolving 10.0 g CMC in 500 ml deionized water. The CMC stock solution was acidified by adding 2100 μl concentrated HCl to decrease the pH of the casting solution to 3.37.

A 50% CMC/50% PEO (8K) membrane was made by mixing 40.07 g of the CMC stock solution with 40.06 g of the PEO (8K) stock solution. The casting solution was acidified to a pH of 3.46. A 50% CMC/50% PEO (300K) membrane was made by mixing 39.99 g of the CMC stock solution with 40.31 g of the PEO (300K) stock solution and adding sufficient HCl to lower the pH to 3.45. A 50% CMC/50% PEO(900K) membrane was made by mixing 39.22 g of the CMC stock solution with 39.63 g of the PEO (900K) stock solution and adding sufficient HCl to lower the pH to 3.56. A 50% CMC/50% PEO (5M) membrane was made by mixing 38.61 g of the CMC stock solution with 40.00 g of the PEO (5M) stock solution and adding sufficient HCl to lower the pH to 3.55.

Membranes made from these various acidified CMC/PEO mixtures were cast and dried according to the methods given in Example 1. FIG. 7 shows the effect of the molecular weight of PEO on the hydration ratios of the resulting membranes. The results indicate that increasing the molecular weight of PEO increases the hydration ratio, although there was little increase in hydration by increasing the PEO molecular weight from 900 kd to 5000 kd. Further differences between the membranes made from various molecular weights of PEO's can be observed from the data presented in FIGS. 4–6.

Example 5

Membranes Of Different Molecular Weight CMC

A 50% CMC/50% PEO membrane was made from CMC (type 7MF PH; lot FP10 12939, obtained from the Aqualon Division of Hercules, Wilmington, Del.) and PEO with a molecular weight of 900,000 (Union Carbide). In contrast to the "high viscosity", type 7HF CMC, the 7 MF CMC has a much lower viscosity in solution. The average molecular weight of type 7 MF is approximately 250 kd as compared to 700 kd for the 7HF type CMC. 5.0 g of CMC and 5.0 g of PEO (900K) were pre-blended dry and then dissolved in 500 ml deionized water according to the methods of Example 1. The solution was acidified with 950 μL of concentrated HCl which reduced the pH to 3.48. A membrane made from 20.0 g stock casting solution. Other portions of the stock solution were used to make more acidic membranes (with casting solutions pH's of 3.07, 2.51, and 1.96). The membranes were cast and dried from these acidified solutions. After drying, the hydration ratio, mass loss, and acid load were determined as previously described. See Table 6.

TABLE 6

Properties of Low Molecular Weight CMC

| Membrane pH 50% CMC (7MF)/ 50% PEO (900 kd) | Mass Loss (%) | Hydration Ratio (%) | PBS Solution pH |
|---|---|---|---|
| 3.48 | dissolved | not determined | 5.93 |
| 3.07 | dissolved | not determined | 5.33 |
| 2.51 | dissolved | not determined | 5.20 |
| 1.96 | 60 | 343 | 4.33 |

When placed in PBS solution for 5 days (the "acid load" test, see above), each of the membranes lowered the pH of the PBS solutions. The 3 higher pH membranes lost there sheet-like structure and turned into an amorphous, diffuse gel. Only the most acidic membrane maintained its structural integrity. Comparing this membrane with others (FIG. 5) shows that at a pH of 2.0, the membrane made of lower molecular weight CMC was the most soluble. Thus, the strength of the association complex is dependent upon the molecular weight of the CMC.

Example 6

CMC/PEO Membranes With A Different Degree Of CMC Substitution

CMC/PEO membranes were made from CMC of type 99-12M31XP (lot FP10 12159, degree of substitution (d.s.) of 1.17, obtained from the Aqualon Division of Hercules, Wilmington, Del.) and from PEO with a molecular weight of 300,000 (Union Carbide). 200 ml of blended polymer solution was acidified with 600 µl of concentrated HCl to yield a stock solution with a pH of 4.07. 20.7 g of this casting solution was poured into a petri dish; the membrane was dried as described in Example 1. The rest of the stock solution was used to make membranes with increased acidity. The pHs of the casting solutions for those membranes were 3.31, 3.03, 2.73, 2.44, and 2.17, respectively.

FIGS. 4–6 show the properties of these membranes compared to others with different compositions of CMC and PEO. FIG. 4 shows that the hydration ratio of CMC with a degree of substition of 1.12 ($\oplus$) is similar to that of other CMC/PEO membranes with a hydration ratio of 836% water when placed in PBS for 4 days. However, there are differences in other measured properties. FIG. 5 shows that compared to the other membranes, the membranes made from CMC with the higher degree of substitution produce the most soluble membranes. FIG. 6 shows that membranes made from highly substituted CMC produce membranes which deliver the largest acid load to PBS. This is consistent with the idea that at any given pH, there are more hydrogen ions available for dissociation in these membranes made with higher d.s.

Example 7

Ammonia Conditioning Of Membranes

To study the effects of alkali conditioning on CMC/PEO membranes, 3 pieces of dried membranes (approximately 160 mg, composition: 80% CMC (7HF PH)/20% PEO (300K or 5000 kd) were placed in a petri dish. 30 ml of 0.5 N ammonium hydroxide (made from 10×dilution of 5 N ammonia, LabChem, Pittsburgh, Pa.) was added, immersing the membranes. Once completely immersed, the membranes were allowed to soak for either 1 or 5 min. The membranes were then removed from the ammonia solution, the excess ammonia was blotted off with filter paper, and the membranes were placed in a gravity convection oven at 45° C. and allowed to dry. After drying and re-equilibrating at room temperature, the membrane's mass was determined. After drying, the membranes hydration ratio, acid load, and solubility were determined. Results are shown in Table 7.

TABLE 7

Effect of Ammonia Conditioning On CMC/PEO Membranes

| Membrane Composition 80% CMC/ 20% PEO | Treatment Control or 0.5 N NH$_3$ | Hydration Ratio (%) | PBS pH; at 4 d | Mass Loss after NH$_3$ (%) | Mass Loss after PBS (4d) (%) | Total Mass Loss (%) |
|---|---|---|---|---|---|---|
| 300 kd PEO pH 2.03 | Control | 258 | 4.33 | — | 29 | 29 |
|  | 1 min | 374 | 7.29 | 22 | 1 | 23 |
|  | 5 min | 368 | 7.29 | 22 | 0 | 22 |
| 300 kd PEO pH 2.45 | Control | 281 | 3.92 | — | 26 | 26 |
|  | 1 min | 551 | 7.23 | 21 | 7 | 28 |
| 5000 kd PEO, pH 3.1 | Control | 553 | 4.24 | — | 36 | 36 |
|  | 1 min | 4774 | 6.98 | 21 | 61 | 63 |

Table 7 shows that ammonia treatment substantially decreased the acid load delivered to a PBS solution. By extension, this effect would also decrease the acid load delivered to a tissue in vivo. Also, compared to other membranes delivering the same acid load to the PBS other solutions, ammonia-conditioned membranes have lower solubility, and thus, increased residence time in vivo. Therefore, it is possible to introduce antiadhesion membranes with long residence times which deliver little residual acid to tissues. In contrast, unconditioned membranes at a pH of approximately 7.0 rapidly disintegrate, and thus are of little value in preventing post surgical adhesions.

Treating the membrane after initial manufacture reduced the acid load of the membrane. Compared to the controls (not soaked in ammonia) in all cases the conditioning treatment increased the pH from approximately 4 to more neutral pH values. Compared to the controls, the conditioning treatment also increased the hydration ratio of the membranes. Whereas this hydration increase was relatively small for the two types of acidic membranes, the least acidic (pH 3.1 80% CMC/20% PEO (5M)) membrane swelled to a higher degree. The effect of the treatment therefore is dependent on the prior condition of the membrane. The total mass loss due to the ammonia conditioning in two cases (for the 80% CMC/20% PEO (300 kd) pH 2.03 membranes) is slightly lower than that of the controls. This unexpected result may be due to the initial loss of salt in the ammonia solution followed by a uptake of salt in the salt-depleted membranes during soaking in PBS.

Example 8

Conditioning Membranes Using Phosphate Buffer

Similar to Example 7, membranes were conditioned after manufacture in phosphate buffer (50 mM, pH 7.40). A piece of dry membrane (0.163 g; 80% CMC (7 HF PH)/20% PEO (5000 kd), pH 3.1) was placed in a petri dish. The membrane was soaked for 5 min in 30 ml of monobasic potassium phosphate/sodium hydroxide buffer (50 mM, pH 7.40; Fisher Scientific). After 5 minutes the membrane was removed from the solution, excess buffer blotted off with filter paper, and the membrane was placed in a gravity convection oven at 45° C. to dry. After drying and re-equilibration at room temperature, the membrane's mass was 1.42 g (i.e., 13% mass loss). Other membranes were soaked for 20 or 60 minutes in buffer before drying. After drying, the membranes were tested as above. The hydration ratio, acid load, and solubility (after 4 days in PBS) for each of those membranes was determined, and the results are shown in Table 8.

TABLE 8

Effect Of Phosphate Buffer Conditioning On CMC/PEO Membranes

| Membrane Composition 80% CMC/ 20% PEO | Treatment | Hydration Ratio (%) | PBS ph (3 d) | Mass Loss After PO$_4$ (%) | Mass Loss After PBS (3 d) (%) | Total Mass Loss (%) |
|---|---|---|---|---|---|---|
| PEO (300 kd) pH 2.03 | Control | 258 | 4.33 | — | 29 | 29 |
|  | 5 min | 296 | 5.92 | 20 | 10 | 30 |
| PEO (5000 kd) pH 3.1 | Control | 553 | 4.24 | — | 36 | 36 |
|  | 5 min | 572 | 6.58 | 13 | 18 | 31 |
|  | 20 min | 685 | 7.17 | 16 | 19 | 35 |
|  | 60 min | 833 | 7.30 | 20 | 17 | 37 |

Table 8 shows that like ammonia conditioning, phosphate buffer conditioning neutralized the acid load delivered to the PBS solution. Moreover, increasing the duration of exposure to phosphate buffer resulted in progressive neutralization of the acid in the membranes. The pH increased from approximately 4.3 to 7.30 after 1 hour incubation. These membranes remain intact in PBS for at least 3 days. In contrast, membranes made at an original pH of 7.0 and above hydrated rapidly as and completely dissociated and lost integrity within several hours. Thus, conditioning acidic membranes with alkali or neutral phosphate buffer can decrease membrane solubility (increase residence time in vivo) while maintaining a highly biocompatible pH. Further, it is anticipated that soaking acidic membranes in other neutral or alkaline buffer solutions (e.g., a pH 9.0 boric acid-KCl, NaOH, 0.1 M; Fischer Scientific) will also be effective in reducing the acidity of an originally membrane.

Example 9

Conditioning Membranes Using PBS

To determine whether an isotonic, phosphate buffered saline solution can reduce the acid load delivered by a membrane, we repeated the above experiment as in Example 8, but using PBS as the buffer(10 mM, pH 7.4, 3 washes, 20 min each). A piece of dry membrane (wt, 0.340 g; composition: 80% CMC (7HF PH)/20% PEO (300 kd); pH of 3.1) was placed in a petri dish containing 50 ml of a phosphate buffered saline (PBS) solution (10 mM, pH 7.40, Sigma Chemical Company, St. Louis, Mo.) and allowed soak for 20 min. The soaking procedure was repeated another 2 times by decanting the solution from the membrane and adding fresh PBS. Next, the membrane was removed from the PBS solution, blotted and dried as above. After drying and re-equilibrating at room temperature, the membrane's mass was 0.274 g. (a 19.4% mass loss). After drying, the hydration ratio, acid load, and solubility were determined as above. Results are shown in Table 9.

TABLE 9

Effect of Phosphate Buffered Saline Conditioning on CMC/PEO Membranes

| Membrane pH 80% CMC/ 20% PEO (300 kd) | Treatment | Hydration Ratio (%) | PBS pH (3 d) | Mass Loss After PBS Conditioning (%) | Mass Loss After PBS (3 d) (%) | Total Mass Loss (%) |
|---|---|---|---|---|---|---|
| 3.72 | PBS | 3230 | 7.0 | 20 | 53 | 73 |
| 3.14 | PBS | 1295 | 6.02 | 19 | 37 | 56 |
| 2.85 | Control | 362 | 4.28 | — | 32 | 32 |
| 2.35 | PBS | 417 | 5.26 | 24 | 9 | 33 |
| 1.84 | PBS | 267 | 5.14 | 23 | 2 | 25 |

As with phosphate buffer, conditioning acidic membranes with PBS raises the membrane pH without completely disrupting the strong association between polymers that originally existed at the lower pH. Thus, an original membrane of pH 3.14, when conditioned using the PBS buffer method and subsequently placed in PBS, generated a pH of 6.02. A non-conditioned membrane which generates the same pH in PBS would originally have a pH in the range of 3–4. Additionally, except for pHs below 2, the conditioned membranes hydrate to a higher degree than un-conditioned membranes. Thus, the conditioned membranes retain some properties of the original, acidic membranes, yet are more biocompatible due to the decreased acid load delivered in solution.

Example 10

Multilayered CMC/PEO Membranes

To provide membranes with more varied properties, membranes were made by sandwiching an acidified membrane between two layers of a neutral membrane, the latter of which may or may not have the same CMC/PEO ratio as the acidified membrane. A sheet of partially dried neutral membrane was first placed on a dry flat surface used as the drying surface for the laminated membrane. A sheet of partially dried acidified membrane of slightly smaller dimensions was carefully placed on the neutral membrane. Next, another sheet of partially dried membrane was carefully placed over the acidified membrane such that the edges of the two neutral membranes were aligned and that none of the acidified membrane extended beyond the edges of the two neutral membranes. When all the three sheets were properly aligned, deionized water was slowly introduced into the petri dish, with care being taken not to misalign the sheets relative to one another. When all sheets were wetted, a non-absorbable porous thin membrane such as a nylon filter medium was carefully placed over the wetted laminate and only slightly pressed onto it. This assembly was then left undisturbed until it is dry, at which point the porous membrane was carefully removed followed by removal of the laminated membrane from the flat surface.

An alternative, double-layered membrane was made in a similar fashion. The bi-layered membrane exhibits different properties on each side. The low pH side, which is more poorly bioadhesive, permits that side to slide more easily over a tissue than the side with higher pH. The side with higher pH would adhere more strongly to the tissue in contact with it and conform to the crevices in the tissue better keeping it in place. Such membranes are valuable in situations where a mobile tissue normally can move freely with respect to a more fixed tissue.

Another bi-layered membrane was made by placing a partially dried membrane (ratio of CMC:PEO=95:5, pH 3.0, cast from 15 gm of a 2% polymer solution) in a petri dish and then pouring a CMC/PEO (ratio of CMC:PEO=95:5, pH 5.5, cast from 10 gm of a 2% polymer solution) mixture on top of the partially dried membrane. The mixture and partially dried membrane were then dried together to form the final, bi-layered membrane. In a similar way, bilayered membranes of varying PEO compositions were made, e.g., membranes in which the two layers have different PEO contents. The higher the PEO content of the layer, the more slippery the surface of that layer becomes. The other layer, with lower PEO content, adheres more strongly to the tissue.

An example is abdominal surgery, where the intestinal membranes move freely with respect to each other and to the surrounding abdominal peritoneum. Additional examples involve thoracic surgery, where the lungs must be able to move with respect to the surrounding peritoneum. Placing the high pH side of a membrane against the parietal peritoneum will keep it in place but will permit the visceral peritoneum attached to the lungs to move freely. Similarly, in cardiac surgery, placing the high pH side of a bilayered membrane onto the pericardium will keep the membrane in place and permit the low pH side to slide more freely over cardiac tissues, for example, the myocardium. Similarly, in orthopedic surgery, placing the high pH side of a membrane against a fixed tissue, such as bone or periosteum, will cause it to adhere more firmly to those locations and permit a less fixed tissue, such as a ligament, tendon, or muscle, to move more freely.

Example 11

Effect of Concentration of CMC/PEO On Stability Of Casting Solutions

To determine the effects of the CMC and PEO concentrations on the stability of casting solutions, we added 16 g of CMC d.s.=1.2. and 4 g PEO (300 kd) to 50 ml isopropanol to make a slurry, which was then added to 450 ml water. This resulted in a relatively homogeneous but more viscous casting solution than that of Examples 1–10. A series of membranes were made by acidifying portions of the casting solution to progressively lower pHs. 11 g portions of the casting solution were poured into 10 cm petri dishes and dried.

Membranes were homogeneous above pH of about 3.3, whereas the association complexes precipitated from the casting solution at lower pH. At lower membrane pH, the resulting membranes had areas of inhomogeniety and holes, and had rough surfaces.

Membranes can be made from solutions of CMC as high as 10% by weight and of PEO as high as 20% by weight.

Example 12

Antithrombogenic effect of CMC/PEO Membranes

Samples of CMC (7 HF PH) and CMC/PEO (5000 kd) membranes were made with CMC/PEO ratios of 80%/20%, 65%/35%, and 50%/50%. An observation chamber for adherent platelets was assembled consisting of a polymer-coated glass slide, two polyethylene spacers, and a glass coverslip. Human blood, obtained from healthy adult volunteers after informed consent, was collected in heparin-containing evacuated containers (Vacutainers™, Becton-Dickinson, Rutherford, N.J.). Heparinized blood was centrifuged at 100 g for 10 min to obtain platelet-rich plasma (PRP).

Two hundred $\mu$l of PRP was instilled into the platelet observation chamber. Platelets in PRP were allowed to adhere and activate on the polymer surfaces for 1 hr at room temperature. Non-adherent platelets and plasma proteins were removed by washing the chamber with PBS. Adherent platelets were fixed with 2.0% (w/v) glutaraldehyde solution in PBS for 1 hour. After washing with PBS, the platelets were stained with 0.1% (w/v) Commassie Brilliant Blue (Bio-Rad, Hercules, Calif.) dye solution for 1.5 hours. Stained platelets were observed using a Nikon Labophot™ II light microscope at 40×magnification (Melville N.Y.). The image of adherent platelets was transferred to a Sony Trinitron™ video display using a Mamamatsu CCD™ camera (Hamamatsu-City, Japan). The Hamamatsu Argus-10™ image processor was used to calculate the number of platelets per 25,000 $\mu m^2$ surface area in every field of observation. The extent of platelet activation was determined qualitatively from the spreading behavior of adherent platelets. Images of activated platelets were obtrained from the Sony Trinitron™ video display screen using a Polaroid Screen-Shooter™ camera (Cambridge, Mass.).

The number of adherent platelets and the extent of platelet activation are considered early indicators of the thrombogenicity of blood-contacting biomaterials. Platelet activation was measured qualitatively by the extent of platelet spreading on the polymer surfaces. The extent of platelet spreading was judged from 1 (least reactive) to 5 (most reactive) as described in Table 10.

TABLE 10

Evaluation of Platelet Activation: Surface-Induced Spreading

| Platelet Activation Stage | Approximate Spread Area ($\mu m^2$) | Remarks |
|---|---|---|
| 1 | 10–15 | Contact-adherence. Platelets not active. |
| 2 | 15–25 | Partially active. Initiation of pseudopods. |
| 3 | 25–35 | Partially activated. Pseudopod extension and initiation of release of granular contents. |
| 4 | 35–45 | Partially activated. Significant pseudopod formation and extension. Complete release of granular contents. |
| 5 | >45 | Fully activated. Retraction of pseudopods leading to the flat or "pancake" shape. |

TABLE 11

Platelet Adherence And Activation By CMC/PEO Membranes

| Membrane Composition | Number of Adherent Platelets (per 25,000 $\mu m^2$)[a] | Extent of Activation |
|---|---|---|
| 100% CMC | 95.8 ± 15.3 | 2.96 ± 0.37 |
| 80% CMC/20% PEO | 48.1 ± 10.9 | 3.25 ± 0.35 |
| 65% CMC/35% PEO | 17.8 ± 4.25 | 1.57 ± 0.39 |
| 50% CMC/50% PEO | 5.25 ± 2.67 | 1.00 ± 0.00 | a: mean ± standard deviation (n = 24).

Table 11 shows that significant number of platelets had adhered and activated on membranes made of 100% CMC. On the average, more than 95 activated platelets were present per 25,000 $\mu m^2$. The number of adherent platelets and the extent of activation decreased with increasing PEO content in the membranes. The CMC/PEO 50%/50% membranes had the least number of platelets. On the average, only 5.0 contact-adherent platelets were present on these membranes.

The results of this study indicate that CMC/PEO membranes, especially the 50%/50% CMC/PEO membrane, is highly anti-thrombogenic, based on the reduction in the number of adherent platelets and the extent of platelet activation on these surfaces. Thus, increasing the amount of PEO in membranes increases their antithrombogenic properties.

To determine whether CMC and PEO adversely affect blood clotting in vivo, we performed a series of studies in which we injected rabbits with CMC/PEO mixtures, and measured prothrombin time.

Four rabbits (2.4 to 2.8 kg) were anesthetized using ketamine (40 mg/kg) and xylazine (8 mg/kg), and 0.20 ml of clinical grade 2% CMC, 0.05% PEO, 50% $H_2O$ and 47.9% balanced salt solution (Lot #SD011089) was injected into the lower spinal area using a 27-gauge, ½ inch needle. A fifth, uninjected rabbit (2.8 kg) served as the control. Blood samples (approximately 1.6 ml) were taken at 0 (before injection), 2, 6, 24, 48, and 96 hr postdose. To 1.6 ml of the collected blood, 0.2 ml of 3.8% sodium citrate solution was added. After mixing plasma was prepared by centrifuging the sample at 2000 rpm for 3 to 5 minutes in a clinical centrifuge. Plasma was pipetted into a separate labeled tube and kept on ice. The sample was frozen and sent to California Veterinary Diagnostics, Inc., West Sacramento, Calif. for prothrombin-time determination, which was conducted in compliance with FDA's Good Laboratory Practice Regulations.

Table 12 shows the prothrombin times for each sample of rabbit plasma at various sampling times. Rabbit blood coagulates more quickly than human blood (Didisheim et al., *J. Lab. Clin. Med.* 53, 866–1959); thus, several of the samples collected from these rabbits coagulated before analysis. However, the samples assayed showed no effect of the CMC/PEO mixture on the prothrombin time except for rabbit No. 3, which showed a transient increase but recovered by day 4.

TABLE 12

Prothrombin Time (Seconds) of Rabbits Injected with CMC/PEO

| Time (hr) | Rabbit Number | | | | |
|---|---|---|---|---|---|
| | 1 | 2 | 3 | 4 | 5* |
| 0 | 7.2 | 7.2 | 7.1 | 8.4 | 7.1 |
| 2 | — | 7.1 | 7.1 | 7.1 | 7.1 |
| 6 | 7.3 | 7.1 | 7.1 | 7.8 | 7.1 |
| 24 | 7.2 | 7.1 | 10.6 | 7.1 | 8.0 |
| 48 | 7.3 | — | 10.3 | — | — |
| 96 | 6.2 | 6.5 | 6.5 | 6.0 | 6.0 |

*Control rabbit not injected with CMC/PEO.
— indicates that assay was not performed because the sample had coagulated.

Example 13

Determination of Bioadhesiveness of CMC/PEO Membranes

Bioadhesiveness of membranes was determined generally using a peel test described below. Several membranes composed of CMC(7HF PH) and PEO (molecular weight 5000 kd) and varying in acidity were tested for their relative bioadhesiveness using an in vitro test. Fresh, center-cut pork chops purchased from a local store were used as adherends to the membranes. Six thinly cut pork chops were placed in polystyrene bioassay dish (243×243×18 mm) and some water placed in the dish to keep a relatively moist environment. Care was taken to blot off any excess water from the exposed side of the pork chop. Six membranes were cut in a rectangular shape to a mass of 120–130 mg and subsequently placed on six individual pieces of meat with their smooth sides down. The smooth side of the membrane is that side which was attached to the polystyrene surface during the drying process. The other side of the membrane which was exposed to air generally yields a slightly rougher surface. A top cover of polystyrene was placed over the dish and the membranes were allowed to hydrate and adhere to the meat at room temperature for 3 hours. In a similar manner, other bioassay dishes were used to test other membranes.

After the 3 hour incubation period, the membranes and the meat were carefully examined in a qualitative way for clarity (color, transparency), structural character of the membrane, form of the membrane (folding on the meat), blanching, rippling as a result of strong bioadhesion. The adhesion force in gm. was measured quantitatively in a peel test by first attaching a clip to the edge of the membrane, subsequently attaching the clip to a spring scale (0–10 gm or 0–250 gm range) and slowly pulling the membrane off the meat by vertically raising the spring scale. The force in gm. needed to pull the membrane completely free of the meat, or in some cases, to cause a rip in the membrane was recorded.

TABLE 13

Summary: Comparative Adhesion Strength of CMC/PEO Membranes

| Membrane pH | % PEO (5000 kd) in Membrane | | | | | |
|---|---|---|---|---|---|---|
| | 35% | 20% | 10% | 5% | 2.5% | 0 |
| 2.00 | — | 2 | — | — | — | 100 |
| 2.80 | 7 | 7.5a | — | — | — | 0 |
| 3.00 | 9 | 7.5[a] | 7[b] | 120[b] | 50[b] | 9 |
| 3.10 | — | 83[b] | 6[b] | — | — | — |
| 3.30 | — | — | — | >150[b] | 67[b] | 11[b] |
| 4.00 | — | — | 8[c] | 10[c] | 7[c] | 3 |

[a]: mean value: n = 2 ea
[b]: mean value: n = 3 ea
[c]: mean value: n = 4 ea

The results shown in Table 13 show that the adhesion force between CMC/PEO membranes is related to the membrane pH. The pH showing the greatest adhesive force for a given PEO percentage was approximately 3.30, but either increasing or decreasing the pH from this level decreased adhesion force. Further, the adhesion force was related to the % PEO in the membrane. The membranes with the highest PEO percentage exhibited the least adhesion. Increasing the PEO percentage increased adhesion until 5% PEO is reached, but further increases in PEO concentration decreased adhesive force.

Example 14

In Vivo Clearance of CMC and PEO

To determine the in vivo clearance of CMC and PEO, we performed a series of experiments in which we injected rats with radio-labeled CMC and PEO (2% CMC, 0.05% PEO, 50% $H_2O$ and 47.9% balanced salt solution). The studies were conducted under Good Laboratory Practices.

Formulations containing [$^{14}$C]carboxymethylcellulose (CMC) and [$^{14}$C]polyethylene oxide (PEO) were injected into the lower spinal area of four groups of six rats (3 male, 3 female); two groups were sacrificed after 3 days and the remaining two groups after 7 days. Urine and feces were collected daily from these rats to study the excretion pattern of the radioactivity. In addition, representative internal organs were assayed for the residual levels of radioactivity in these rats. Two separate sets of six rats were similarly injected, and blood samples were assayed for radioactivity at 0-time (pre-injection) and 8, 24, 48, 72, 96, and 168 hours after injection.

Both compounds were excreted primiarily in the urine. Most of the excretion in urine occurred during the first 24 hours. In the 7-day study, the half-times for excretion of the $^{14}$C-CMC in the urine and feces were approximately 0.2 day (5 h) initially followed by a longer excretion half-time of approximately 1.6 days. The corresponding values for $^{14}$C-PEO were 0.2 day (5 h) and 1.7 days, respectively. Of the organs assayed, the liver and kidney contained the highest levels of radioactivity. The percentage of the injected dose in the liver was comparable for $^{14}$C-CMC and $^{14}$C-PEO but that in the kidney was at least 6 times higher after injection of $^{14}$C-PEO than after injection of $^{14}$C-CMC.

The radioactivity level in the blood after $^{14}$C-CMC administration declined with half-time of approximately 1 day, whereas the blood half-time for $^{14}$C-PEO was approximately 4 days. Higher percentages of the administered dose remained in the carcass plus injection site for $^{14}$C-CMC than for $^{14}$C-PEO. The mean overall recovery of the administered dose was 80+% for both compounds. No adverse reactions to the injected $^{14}$C-CMC or $^{14}$C-PEO were observed.

Example 15

Bioresorbability of CMC/PEO Membranes

The bioresorbability of CMC/PEO membranes is determined by making a surgical incisions in the rear legs of rats, and placing a portion of a CMC/PEO membrane into a muscular layer. Several membranes of different composition or degree of cross linking are inserted into each animal, after which the incisions are closed. A sufficient number of animals are to be used for each type of membrane to be evaluated. Daily thereafter, animals are sacrificed, the incisions re-opened and the remaining membranes are observed for the degree of intactness, and their locations. Membranes are removed, blotted to remover excess water, weighed while wet, re-dried, and re-weighed. The amounts of fluid absorbed, of solids remaining, and the appearance of the membranes are noted. Comparisons are made between the length of time in situ, tissue location, the membrane composition, pre-insertion conditioning, and the resorbability are made. The membranes of the instant invention are tailored to have a desired degree of bioresorbability.

Example 16

Determination of Antiadhesion Properties of CMC/PEO Membranes

The ability of CMC/PEO membranes to inhibit adhesion formation is determined according to the standard method of Harris et al., Surgery 117(6):663–669, (1995). Adult rats are used. They are anesthetized with intraperitoneal sodium pentobarbital (43 mg/kg) until deep surgical anesthesia was achieved, as determined by absence of pain responses to paw pinching and the absence of eyelid reflexes. They are placed ventral side up, and their abdominal hair is removed, and the skin is cleaned using iodophor scrub and rinsed with 70% alcohol.

Under sterile conditions, a 6 cm long ventral midline incision is made and the skin retracted. A 4 cm long midline incision is made in the abdominal wall, and the right abdominal was is reflected. A 1 by 2 cm segment of the parietal peritoneum is excised, including a superficial layer of underlying muscle, 1 cm lateral to the midline incision. The caecum is then elevated so that at closure, the caecum would make contact with the abdominal wall. Several areas of the caecum are gently abraded using a sterile, scalpel blade so that a homogenous surface of petechial hemorrhages are created. The reflected abdominal wall is also abraded, and the abraded areas exposed to air for 10 minutes.

Apposing portions of caecum and abdominal wall are either placed in contact with each other, or are apposed with each other with a measured amount of an antiadhesion membrane placed between them. After covering the abraded areas, the surgical incisions were closed. 3 days to 4 weeks later, the animals are sacrificed using excess anesthetic, and the sites of surgery exposed.

Adhesions are graded according to the method of Becker et al., *J. Amer. Coll. Surgeons* 183(4):297–306 (1996) from 0 to 3, with 0 being no detectable adhesions, 1 having filmy thickness, avascular, grade 2 having moderate thickness and limited vascularity, and grade 3 having dense thickness and being well vascularized. Other methods of grading adhesions may be used. (E.g., Diamond, *Fertility and Sterility* 66(6):904–910 (1996); Interceed (TC7) *Adhesion Study Group, Fertility and Sterility* 51(6):933(1989).

The bioresorbability of the membranes is determined at the time of sacrifice by palpating the surgical sites and determining the presence or absence of intact membrane. If intact membrane is present, it will be removed from the site, and wet and dry weights will be determined. The membranes of the invention are tailored to exhibit desired antiadhesion properties.

Types of Surgery

Any type of surgical procedure benefits from the use of the membranes of the present invention. The following are exemplary, and are not intended to be limiting.

Example 17

Cranial Surgery

For craniotomy use, membranes of the present invention are used as a dural replacement graft following skull trephination and dural excision. The membrane is placed on the exposed cortex. The replacement of bone, closure of soft tissues and scalp completes the operation. The membrane forms a barrier to adhesion formation between the cortex and the skull and a scaffold to effect early ingrowth necessary for dural repair.

Example 18

Ocular Surgery

Ocular uses include surgery for glaucoma filtering. Successful glaucoma filtering surgery is characterized by the passage of aqueous humor from the anterior chamber through a surgically created fistula to the subconjunctival space, which results in the formation of a filtering bleb. Bleb failure most often results from fibroblast proliferation and subconjunctival fibrosis. To prevent this fibrosis, a membrane of the present invention can be placed post-operatively in the subconjunctiva in the bleb space and a membrane also placed in the fistula.

Example 19

Musculoskeletal Surgery

Repair of tendon flexors can be enhanced by using membranes of the present invention, In tendon repair, collagen secreted by fibroblasts unites the ends of tendons. Adhesion formation usually binds the tendon to other tissue structures, obliterating the normal space between the tendon and tendon sheath, thereby interfering with the gliding function necessary for smooth movement. To prevent adhesions from forming between the tendon and the sheath, a membrane of the present invention is wrapped around the reattached sutured tendon ends and/or a hydrogel form of the present invention is injected within the sheath.

For lumbar laminectomy and discectomy, a midline incision is made into the lumbodorsal fascia just lateral to the bulbous tips of the spinous process. The paraspinous facia is opened to expose the interlaminar area of the affected intervertebral disc. A laminectomy is performed to expose the ligamentum flavum which is opened, exposing the dura. The dura is retracted medially and the nerve root is identified and retracted. The disc area is exposed and explored with a nerve hook. The texture of the annulus, amount of bulge, presence of hernias or presence of a hole in the annulus is determined. Disc removal is usually performed through a small hole in the annulus. Post-surgical adhesions are prevented by injecting a hydrogel form of the present invention into the space around the annulus, nerve root, dura and laminectomy defect at the conclusion of the procedure, before closing.

Example 20

Abdominal Surgery

Post-surgical adhesions are reported to form in up to 93% of previously operated laparotomy patients. A laparotomy is required to gain access to the abdomen for large and small intestine procedures, stomach, esophageal, and duodenal procedures, cholecystectomy and operations on the female reproductive systems. In 1992, the Center for Health Statistics reported 344,000 operations in the United States for lysis of peritoneal adhesions. Peritoneal adhesions become pathologic when they anatomically distort abdominal viscera producing various morbidities ranging from intestinal obstruction and volvulus to infertility. Unfortunately, adhesion reformation and recurrence of intestinal obstruction following surgical division of adhesions is fairly common.

To prevent do novo adhesion formation or adhesion reformation, membranes of the present invention are placed directly over or wrapped around the surgical site separating this site from the omentum. When closing, membranes of the present invention are placed under the midline incision between the fascia and peritoneum. In laparoscopic procedures, a hydrogel form of the present invention is used to coat the surgical site and trocar entry areas.

Example 21

Gynecological Surgery: Myomectomy via Laparotomy or Laparoscopy

The uterus is exposed and incised to remove the fibroid. The uterus is closed with absorbable sutures. Posterior uterine incisions are associated with more and a higher degree of adnexal adhesions than that with fundal or anterior uterine incisions. For posterior incisions, apply membranes of the present invention over the posterior uterine incision and beneath the anterior abdominal wall incision in order to prevent adhesion formation between the uterus and surrounding tissues. Anterior incisions more commonly result in adhesion formation between the bladder an anterior wall of the uterus. Membranes of the present invention are placed over the anterior incision and between the uterus and bladder.

Example 22

Thoracic Surgery: Cardiac Procedures

Reoperative cardiac surgical procedures are becoming more commonplace and result in the need to reduce or prevent postoperative mediastinal and pericardial adhesions. A median sternotomy precedes a midline pericardiatomy. The pericardium is suspended, so that the heart and pericardial space are widely exposed. Dissection is performed. To create the bypass, distal anastomoses are constructed using internal mammary arteries, radial arteries, gastroepiploic arteries or saphenous vein grafts. In order to prevent adhesion formation, membranes of the present invention are wrapped around the anastomoses and placed between the pericardium and sternum before closing.

Other features, aspects and objects of the invention can be obtained from a review of the figures and the claims. All citations herein are incorporated by reference in their entirety.

It is to be understood that other embodiments of the invention can be developed and fall within the spirit and scope of the invention and claims.

We claim:

1. A method for preparing an association complex of CPS and PE comprising the steps of:
   a) forming a solution of CPS and PE having a pH in the range of about 3.5 to about 6.0;
   b) allowing the solution to dry thereby forming a dried from of the association complex; and
   c) increasing the pH of the dried complex.

2. The method of claim 1, wherein in the step of increasing the pH increases the pH to about 6.0.

3. The method of claim 1, wherein the step of increasing the pH includes the use of a phosphate buffer to raise the pH to at least 6.0.

4. The method of claim 1, wherein the solution of CPS and PE is a casting solution and forming step includes forming a membrane.

5. A method for preparing an association complex for implantation at a surgical site in order to prevent adhesion, comprising the steps of:
   a) forming a solution comprising CPS and a PE;
   b) acidifying said solution to a pH in the range of about 3.5 to about 6.0 in order to increase the residence time at the surgical site;
   c) allowing the acidic association complex to at least partially dry; and
   d) increasing the pH of the at last partially dried association complex in order to increase biocompatability.

6. A composition comprising an acidified association complex of CPS and PE which has been at least partially dried and made less acidic.

7. The method of claim 5, wherein the CPS is CMC and the PE is PEO.

8. The association complex of claim 6, wherein the CPS is CMC and the PE is PEO.

9. The association complex of claim 1 dried into a flexible membrane.

10. An association complex of CPS and PE having a pH in the range of about 3.5 to about 6.0.

11. The complex of claim 10, wherein the degree of substitution of the CPS is above 0.5.

12. The complex of claim 10, wherein the degree of carboxyl substitution of the CPS has been increased in order to increase bioadhesiveness.

13. The complex of claim 10, which is bioresorbable.

14. The complex of claim 13 which persists in an animal for at least 48 hours but less than 29 days.

15. The complex of claim 10, wherein said complex is bioadhesive and wherein the degree of substitution of the CPS is in the range of greater than about 0 to about 3.0 and/or the amount of PE is in the range of about 90% to about 5%.

16. A method of reducing post-surgical adhesions, comprising the steps of
   a) accessing a delivery site; and
   b) delivering to the delivery site an association complex made of a CPS and a PE having a pH in the range of about 3.5 to about 6.0, wherein the association complex has at least one property selected from the group consisting of bioresorbability, bioadhesiveness, antithrombogenicity, and antiadhesion.

17. The method of claim 16, wherein the delivery site is selected from the group consisting of orthopedic, gastrointestinal, abdominal, thoracic, cranial, cardiovascular, gynecological, arthroscopic, urological, dermal, subdermal, and musculoskeletal.

18. A method of manufacturing an association complex of CPS and PE, consisting essentially of the following steps:
   a) selecting an aqueous solution of a CPS and an aqueous solution of a PE;
   b) mixing said solution of the CPS with said solution of the PE, forming a mixed solution of the CPS and the PE; and
   c) adjusting the pH of the mixed solution of the CPS and the PE to within the range of about 3.5 to about 6.0.

19. An association complex made of a CPS and a PE comprising from about 10% to about 95% CPS and from about 5% to about 90% PE, and made from a solution having a pH in the range of about 3.5 to about 6.0.

20. The association complex of claim 10 further comprising a drug.

21. The association complex of claim 20, wherein the drug is selected from the group consisting of antibiotics, anti-inflammatory drugs, hormones, chemotactic factors, analgesics, and anesthetics.

22. An association complex of a CPS and a PE that possesses one or more of the properties selected from the group consisting of (1) a molecular weight of the CPS in the range of about 100 kd to about 10,000 kd, (2) a molecular weight of the PE in the range of about 5 kd to about 8,000 kd, (3) a degree of substitution of the CPS in the range of greater than about 0 to about 3.0, (4) a percentage of the CPS in the range of about 10% to about 95%, (5) a percentage of PE in the range of about 5% to about 90%, and (6) a pH in the range of about 3.5 to about 6.0.

23. The method of claim 1, wherein the step of increasing the pH includes use of a solution less acidic than said solution of CPS and PE to raise the pH.

24. An association complex made of a CPS and a PE having a pH in the range of about 3.5 to about 6.0, wherein the association complex has at least one property selected from the group consisting of bioresorbability, bioadhesiveness, antithrombogenicity, and antiadhesion.

* * * * *